United States Patent
Turner et al.

(10) Patent No.: US 11,116,415 B2
(45) Date of Patent: Sep. 14, 2021

(54) USE OF BODY-WORN RADAR FOR BIOMETRIC MEASUREMENTS, CONTEXTUAL AWARENESS AND IDENTIFICATION

(71) Applicant: BRAGI GmbH, Munich (DE)

(72) Inventors: Jake Berry Turner, Munich (DE); Peter Vincent Boesen, Munich (DE); Nazli Deniz Cagatay, Munich (DE)

(73) Assignee: BRAGI GMBH, Munich (DE)

(*) Notice: Subject to any disclaimer, the term of this patent is extended or adjusted under 35 U.S.C. 154(b) by 484 days.

(21) Appl. No.: 15/997,511

(22) Filed: Jun. 4, 2018

(65) Prior Publication Data

US 2018/0353086 A1 Dec. 13, 2018

Related U.S. Application Data

(60) Provisional application No. 62/516,476, filed on Jun. 7, 2017.

(51) Int. Cl.
| | |
|---|---|
| *A61B 5/0265* | (2006.01) |
| *G01S 13/50* | (2006.01) |
| *G01S 13/86* | (2006.01) |
| *G01S 7/41* | (2006.01) |
| *A61B 5/0205* | (2006.01) |

(Continued)

(52) U.S. Cl.
CPC .......... *A61B 5/0265* (2013.01); *A61B 5/0024* (2013.01); *A61B 5/0205* (2013.01); *A61B 5/05* (2013.01); *A61B 5/117* (2013.01); *A61B 5/6817* (2013.01); *G01S 7/41* (2013.01); *G01S 7/415* (2013.01); *G01S 13/50* (2013.01); *G01S 13/86* (2013.01); *G01S 13/88* (2013.01); *A61B 5/02141* (2013.01); *A61B 5/02405* (2013.01);

(Continued)

(58) Field of Classification Search
CPC ..... A61B 5/0265; A61B 5/0205; A61B 5/117; G01S 7/415; G01S 13/50; G01S 13/86; G01S 7/41
USPC ........................ 342/22; 345/156; 348/51, 744
See application file for complete search history.

(56) References Cited

U.S. PATENT DOCUMENTS

| | | |
|---|---|---|
| 2,325,590 A | 8/1943 | Carlisle et al. |
| 2,430,229 A | 11/1947 | Kelsey |

(Continued)

FOREIGN PATENT DOCUMENTS

| | | |
|---|---|---|
| CN | 204244472 U | 4/2015 |
| CN | 104683519 A | 6/2015 |

(Continued)

OTHER PUBLICATIONS

Fletcher: "Wearable Doppler Radar with Integrated Antenna for Patient Vital Sign Monitoring", 2010, pp. 276-279, MIT Open Access Articles.

(Continued)

*Primary Examiner* — Bo Fan
(74) *Attorney, Agent, or Firm* — Goodhue, Coleman & Owens, P.C.

(57) ABSTRACT

A method for utilizing radar from wireless earpieces includes activating one or more radar sensors of the wireless earpieces, performing radar measurements of a user using the one or more radar sensors of the wireless earpieces, and analyzing the radar measurements to determine pulsatile measurements associated with the user, the analyzing performed using a processor of the wireless earpieces.

8 Claims, 7 Drawing Sheets

(51) Int. Cl.
  *A61B 5/117* (2016.01)
  *A61B 5/00* (2006.01)
  *A61B 5/05* (2021.01)
  *G01S 13/88* (2006.01)
  *A61B 5/08* (2006.01)
  *A61B 5/021* (2006.01)
  *A61B 5/024* (2006.01)
  *G01S 7/02* (2006.01)

(52) U.S. Cl.
  CPC ......... *A61B 5/02444* (2013.01); *A61B 5/0816* (2013.01); *G01S 7/027* (2021.05)

(56) References Cited

U.S. PATENT DOCUMENTS

| | | |
|---|---|---|
| 3,047,089 A | 7/1962 | Zwislocki |
| D208,784 S | 10/1967 | Sanzone |
| 3,586,794 A | 6/1971 | Michaelis |
| 3,696,377 A | 10/1972 | Wall |
| 3,934,100 A | 1/1976 | Harada |
| 3,983,336 A | 9/1976 | Malek et al. |
| 4,069,400 A | 1/1978 | Johanson et al. |
| 4,150,262 A | 4/1979 | Ono |
| 4,334,315 A | 6/1982 | Ono et al. |
| D266,271 S | 9/1982 | Johanson et al. |
| 4,375,016 A | 2/1983 | Harada |
| 4,588,867 A | 5/1986 | Konomi |
| 4,617,429 A | 10/1986 | Bellafiore |
| 4,654,883 A | 3/1987 | Iwata |
| 4,682,180 A | 7/1987 | Gans |
| 4,791,673 A | 12/1988 | Schreiber |
| 4,852,177 A | 7/1989 | Ambrose |
| 4,865,044 A | 9/1989 | Wallace et al. |
| 4,984,277 A | 1/1991 | Bisgaard et al. |
| 5,008,943 A | 4/1991 | Arndt et al. |
| 5,185,802 A | 2/1993 | Stanton |
| 5,191,602 A | 3/1993 | Regen et al. |
| 5,201,007 A | 4/1993 | Ward et al. |
| 5,201,008 A | 4/1993 | Arndt et al. |
| D340,286 S | 10/1993 | Seo |
| 5,280,524 A | 1/1994 | Norris |
| 5,295,193 A | 3/1994 | Ono |
| 5,298,692 A | 3/1994 | Ikeda et al. |
| 5,343,532 A | 8/1994 | Shugart |
| 5,347,584 A | 9/1994 | Narisawa |
| 5,363,444 A | 11/1994 | Norris |
| 5,444,786 A | 8/1995 | Raviv |
| D367,113 S | 2/1996 | Weeks |
| 5,497,339 A | 3/1996 | Bernard |
| 5,606,621 A | 2/1997 | Reiter et al. |
| 5,613,222 A | 3/1997 | Guenther |
| 5,654,530 A | 8/1997 | Sauer et al. |
| 5,692,059 A | 11/1997 | Kruger |
| 5,721,783 A | 2/1998 | Anderson |
| 5,748,743 A | 5/1998 | Weeks |
| 5,749,072 A | 5/1998 | Mazurkiewicz et al. |
| 5,771,438 A | 6/1998 | Palermo et al. |
| D397,796 S | 9/1998 | Yabe et al. |
| 5,802,167 A | 9/1998 | Hong |
| 5,844,996 A | 12/1998 | Enzmann et al. |
| D410,008 S | 5/1999 | Almqvist |
| 5,929,774 A | 7/1999 | Charlton |
| 5,933,506 A | 8/1999 | Aoki et al. |
| 5,949,896 A | 9/1999 | Nageno et al. |
| 5,987,146 A | 11/1999 | Pluvinage et al. |
| 6,021,207 A | 2/2000 | Puthuff et al. |
| 6,054,989 A | 4/2000 | Robertson et al. |
| 6,081,724 A | 6/2000 | Wilson |
| 6,084,526 A | 7/2000 | Blotky et al. |
| 6,094,492 A | 7/2000 | Boesen |
| 6,111,569 A | 8/2000 | Brusky et al. |
| 6,112,103 A | 8/2000 | Puthuff |
| 6,157,727 A | 12/2000 | Rueda |
| 6,167,039 A | 12/2000 | Karlsson et al. |
| 6,181,801 B1 | 1/2001 | Puthuff et al. |
| 6,185,152 B1 | 2/2001 | Shen |
| 6,208,372 B1 | 3/2001 | Barraclough |
| 6,230,029 B1 | 5/2001 | Yegiazaryan et al. |
| 6,275,789 B1 | 8/2001 | Moser et al. |
| 6,339,754 B1 | 1/2002 | Flanagan et al. |
| D455,835 S | 4/2002 | Anderson et al. |
| 6,408,081 B1 | 6/2002 | Boesen |
| 6,424,820 B1 | 7/2002 | Burdick et al. |
| D464,039 S | 10/2002 | Boesen |
| 6,470,893 B1 | 10/2002 | Boesen |
| D468,299 S | 1/2003 | Boesen |
| D468,300 S | 1/2003 | Boesen |
| 6,542,721 B2 | 4/2003 | Boesen |
| 6,560,468 B1 | 5/2003 | Boesen |
| 6,563,301 B2 | 5/2003 | Gventer |
| 6,654,721 B2 | 11/2003 | Handelman |
| 6,664,713 B2 | 12/2003 | Boesen |
| 6,690,807 B1 | 2/2004 | Meyer |
| 6,694,180 B1 | 2/2004 | Boesen |
| 6,718,043 B1 | 4/2004 | Boesen |
| 6,738,485 B1 | 5/2004 | Boesen |
| 6,748,095 B1 | 6/2004 | Goss |
| 6,754,358 B1 | 6/2004 | Boesen et al. |
| 6,784,873 B1 | 8/2004 | Boesen et al. |
| 6,823,195 B1 | 11/2004 | Boesen |
| 6,852,084 B1 | 2/2005 | Boesen |
| 6,879,698 B2 | 4/2005 | Boesen |
| 6,892,082 B2 | 5/2005 | Boesen |
| 6,920,229 B2 | 7/2005 | Boesen |
| 6,952,483 B2 | 10/2005 | Boesen et al. |
| 6,987,986 B2 | 1/2006 | Boesen |
| 7,010,137 B1 | 3/2006 | Leedom et al. |
| 7,113,611 B2 | 9/2006 | Leedom et al. |
| D532,520 S | 11/2006 | Kampmeier et al. |
| 7,136,282 B1 | 11/2006 | Rebeske |
| 7,203,331 B2 | 4/2007 | Boesen |
| 7,209,569 B2 | 4/2007 | Boesen |
| 7,215,790 B2 | 5/2007 | Boesen et al. |
| D549,222 S | 8/2007 | Huang |
| D554,756 S | 11/2007 | Sjursen et al. |
| 7,403,629 B1 | 7/2008 | Aceti et al. |
| D579,006 S | 10/2008 | Kim et al. |
| 7,463,902 B2 | 12/2008 | Boesen |
| 7,508,411 B2 | 3/2009 | Boesen |
| 7,532,901 B1 | 5/2009 | LaFranchise et al. |
| D601,134 S | 9/2009 | Elabidi et al. |
| 7,825,626 B2 | 11/2010 | Kozisek |
| 7,859,469 B1 | 12/2010 | Rosener et al. |
| 7,965,855 B1 | 6/2011 | Ham |
| 7,979,035 B2 | 7/2011 | Griffin et al. |
| 7,983,628 B2 | 7/2011 | Boesen |
| D647,491 S | 10/2011 | Chen et al. |
| 8,095,188 B2 | 1/2012 | Shi |
| 8,108,143 B1 | 1/2012 | Tester |
| 8,140,357 B1 | 3/2012 | Boesen |
| 8,204,786 B2 | 6/2012 | LeBoeuf et al. |
| D666,581 S | 9/2012 | Perez |
| 8,300,864 B2 | 10/2012 | Müllenborn et al. |
| 8,406,448 B2 | 3/2013 | Lin et al. |
| 8,430,817 B1 | 4/2013 | Al-Ali et al. |
| 8,436,780 B2 | 5/2013 | Schantz et al. |
| D687,021 S | 7/2013 | Yuen |
| 8,679,012 B1 | 3/2014 | Kayyali |
| 8,719,877 B2 | 5/2014 | VonDoenhoff et al. |
| 8,774,434 B2 | 7/2014 | Zhao et al. |
| 8,831,266 B1 | 9/2014 | Huang |
| 8,891,800 B1 | 11/2014 | Shaffer |
| 8,994,498 B2 | 3/2015 | Agrafioti et al. |
| D728,107 S | 4/2015 | Martin et al. |
| 9,013,145 B2 | 4/2015 | Castillo et al. |
| 9,037,125 B1 | 5/2015 | Kadous |
| D733,103 S | 6/2015 | Jeong et al. |
| 9,081,944 B2 | 7/2015 | Camacho et al. |
| 9,461,403 B2 | 10/2016 | Gao et al. |
| 9,510,159 B1 | 11/2016 | Cuddihy et al. |
| D773,439 S | 12/2016 | Walker |
| D775,158 S | 12/2016 | Dong et al. |
| D777,710 S | 1/2017 | Palmborg et al. |

(56) References Cited

U.S. PATENT DOCUMENTS

| | | |
|---|---|---|
| 9,544,689 B2 | 1/2017 | Fisher et al. |
| D788,079 S | 5/2017 | Son et al. |
| 9,684,778 B2 | 6/2017 | Tharappel et al. |
| 9,711,062 B2 | 7/2017 | Ellis et al. |
| 9,729,979 B2 | 8/2017 | Özden |
| 9,755,704 B2 | 9/2017 | Hviid et al. |
| 9,767,709 B2 | 9/2017 | Ellis |
| 9,813,826 B2 | 11/2017 | Hviid et al. |
| 9,848,257 B2 | 12/2017 | Ambrose et al. |
| 9,949,008 B2 | 4/2018 | Hviid et al. |
| 2001/0005197 A1 | 6/2001 | Mishra et al. |
| 2001/0027121 A1 | 10/2001 | Boesen |
| 2001/0043707 A1 | 11/2001 | Leedom |
| 2001/0056350 A1 | 12/2001 | Calderone et al. |
| 2002/0002413 A1 | 1/2002 | Tokue |
| 2002/0007510 A1 | 1/2002 | Mann |
| 2002/0010590 A1 | 1/2002 | Lee |
| 2002/0030637 A1 | 3/2002 | Mann |
| 2002/0046035 A1 | 4/2002 | Kitahara et al. |
| 2002/0057810 A1 | 5/2002 | Boesen |
| 2002/0076073 A1 | 6/2002 | Taenzer et al. |
| 2002/0118852 A1 | 8/2002 | Boesen |
| 2003/0002705 A1 | 1/2003 | Boesen |
| 2003/0065504 A1 | 4/2003 | Kraemer et al. |
| 2003/0100331 A1 | 5/2003 | Dress et al. |
| 2003/0104806 A1 | 6/2003 | Ruef et al. |
| 2003/0115068 A1 | 6/2003 | Boesen |
| 2003/0125096 A1 | 7/2003 | Boesen |
| 2003/0218064 A1 | 11/2003 | Conner et al. |
| 2004/0070564 A1 | 4/2004 | Dawson et al. |
| 2004/0102931 A1 | 5/2004 | Ellis et al. |
| 2004/0160511 A1 | 8/2004 | Boesen |
| 2005/0017842 A1 | 1/2005 | Dematteo |
| 2005/0043056 A1 | 2/2005 | Boesen |
| 2005/0094839 A1 | 5/2005 | Gwee |
| 2005/0125320 A1 | 6/2005 | Boesen |
| 2005/0148883 A1 | 7/2005 | Boesen |
| 2005/0165663 A1 | 7/2005 | Razumov |
| 2005/0196009 A1 | 9/2005 | Boesen |
| 2005/0197063 A1 | 9/2005 | White |
| 2005/0212911 A1 | 9/2005 | Marvit et al. |
| 2005/0251455 A1 | 11/2005 | Boesen |
| 2005/0266876 A1 | 12/2005 | Boesen |
| 2006/0029246 A1 | 2/2006 | Boesen |
| 2006/0073787 A1 | 4/2006 | Lair et al. |
| 2006/0074671 A1 | 4/2006 | Farmaner et al. |
| 2006/0074808 A1 | 4/2006 | Boesen |
| 2006/0166715 A1 | 7/2006 | Engelen et al. |
| 2006/0166716 A1 | 7/2006 | Seshadri et al. |
| 2006/0220915 A1 | 10/2006 | Bauer |
| 2006/0258412 A1 | 11/2006 | Liu |
| 2007/0102009 A1 | 5/2007 | Wong et al. |
| 2007/0239225 A1 | 10/2007 | Saringer |
| 2007/0269785 A1 | 11/2007 | Yamanoi |
| 2007/0291591 A1* | 12/2007 | Peng .................. G01S 15/104 367/101 |
| 2008/0076972 A1 | 3/2008 | Dorogusker et al. |
| 2008/0090622 A1 | 4/2008 | Kim et al. |
| 2008/0102424 A1 | 5/2008 | Holljes |
| 2008/0146890 A1 | 6/2008 | LeBoeuf et al. |
| 2008/0187163 A1 | 8/2008 | Goldstein et al. |
| 2008/0215239 A1 | 9/2008 | Lee |
| 2008/0253583 A1 | 10/2008 | Goldstein et al. |
| 2008/0254780 A1 | 10/2008 | Kuhl et al. |
| 2008/0255430 A1 | 10/2008 | Alexandersson et al. |
| 2008/0298606 A1 | 12/2008 | Johnson et al. |
| 2009/0003620 A1 | 1/2009 | McKillop et al. |
| 2009/0008275 A1 | 1/2009 | Ferrari et al. |
| 2009/0017881 A1 | 1/2009 | Madrigal |
| 2009/0041313 A1 | 2/2009 | Brown |
| 2009/0073070 A1 | 3/2009 | Rofougaran |
| 2009/0097689 A1 | 4/2009 | Prest et al. |
| 2009/0105548 A1 | 4/2009 | Bart |
| 2009/0154739 A1 | 6/2009 | Zellner |
| 2009/0191920 A1 | 7/2009 | Regen et al. |
| 2009/0226017 A1 | 9/2009 | Abolfathi et al. |
| 2009/0240947 A1 | 9/2009 | Goyal et al. |
| 2009/0245559 A1 | 10/2009 | Boltyenkov et al. |
| 2009/0261114 A1 | 10/2009 | McGuire et al. |
| 2009/0296968 A1 | 12/2009 | Wu et al. |
| 2009/0303073 A1 | 12/2009 | Gilling et al. |
| 2009/0304210 A1 | 12/2009 | Weisman |
| 2010/0033313 A1 | 2/2010 | Keady et al. |
| 2010/0075631 A1 | 3/2010 | Black et al. |
| 2010/0149073 A1* | 6/2010 | Chaum .............. G02B 27/0172 345/8 |
| 2010/0166206 A1 | 7/2010 | Macours |
| 2010/0203831 A1 | 8/2010 | Muth |
| 2010/0210212 A1 | 8/2010 | Sato |
| 2010/0290636 A1 | 11/2010 | Mao et al. |
| 2010/0320961 A1 | 12/2010 | Castillo et al. |
| 2011/0018731 A1 | 1/2011 | Linsky et al. |
| 2011/0103609 A1 | 5/2011 | Pelland et al. |
| 2011/0137141 A1 | 6/2011 | Razoumov et al. |
| 2011/0140844 A1 | 6/2011 | McGuire et al. |
| 2011/0239497 A1 | 10/2011 | McGuire et al. |
| 2011/0286615 A1 | 11/2011 | Olodort et al. |
| 2011/0293105 A1 | 12/2011 | Ade et al. |
| 2012/0057740 A1 | 3/2012 | Rosal |
| 2012/0155670 A1 | 6/2012 | Rutschman |
| 2012/0159617 A1 | 6/2012 | Wu et al. |
| 2012/0163626 A1 | 6/2012 | Booij et al. |
| 2012/0197737 A1 | 8/2012 | LeBoeuf et al. |
| 2012/0235883 A1 | 9/2012 | Border et al. |
| 2012/0309453 A1 | 12/2012 | Maguire |
| 2013/0106454 A1 | 5/2013 | Liu et al. |
| 2013/0154826 A1 | 6/2013 | Ratajczyk |
| 2013/0178967 A1 | 7/2013 | Mentz |
| 2013/0200999 A1 | 8/2013 | Spodak et al. |
| 2013/0204617 A1 | 8/2013 | Kuo et al. |
| 2013/0293494 A1 | 11/2013 | Reshef |
| 2013/0316642 A1 | 11/2013 | Newham |
| 2013/0346168 A1 | 12/2013 | Zhou et al. |
| 2014/0004912 A1 | 1/2014 | Rajakarunanayake |
| 2014/0014697 A1 | 1/2014 | Schmierer et al. |
| 2014/0020089 A1 | 1/2014 | Perini, II |
| 2014/0072136 A1 | 3/2014 | Tenenbaum et al. |
| 2014/0072146 A1 | 3/2014 | Itkin et al. |
| 2014/0073429 A1 | 3/2014 | Meneses et al. |
| 2014/0079257 A1 | 3/2014 | Ruwe et al. |
| 2014/0106677 A1 | 4/2014 | Altman |
| 2014/0122116 A1 | 5/2014 | Smythe |
| 2014/0132390 A1* | 5/2014 | Loveland .............. H05B 47/115 340/5.8 |
| 2014/0146973 A1 | 5/2014 | Liu et al. |
| 2014/0153768 A1 | 6/2014 | Hagen et al. |
| 2014/0163771 A1 | 6/2014 | Demeniuk |
| 2014/0185828 A1 | 7/2014 | Helbling |
| 2014/0219467 A1 | 8/2014 | Kurtz |
| 2014/0222462 A1 | 8/2014 | Shakil et al. |
| 2014/0235169 A1 | 8/2014 | Parkinson et al. |
| 2014/0270227 A1 | 9/2014 | Swanson |
| 2014/0270271 A1 | 9/2014 | Dehe et al. |
| 2014/0276227 A1 | 9/2014 | Pérez |
| 2014/0310595 A1 | 10/2014 | Acharya et al. |
| 2014/0321682 A1 | 10/2014 | Kofod-Hansen et al. |
| 2014/0335908 A1 | 11/2014 | Krisch et al. |
| 2014/0348367 A1 | 11/2014 | Vavrus et al. |
| 2015/0028996 A1 | 1/2015 | Agrafioti et al. |
| 2015/0035643 A1 | 2/2015 | Kursun |
| 2015/0036835 A1 | 2/2015 | Chen |
| 2015/0056584 A1 | 2/2015 | Boulware et al. |
| 2015/0110587 A1 | 4/2015 | Hori |
| 2015/0148989 A1 | 5/2015 | Cooper et al. |
| 2015/0181356 A1 | 6/2015 | Krystek et al. |
| 2015/0230022 A1 | 8/2015 | Sakai et al. |
| 2015/0245127 A1 | 8/2015 | Shaffer |
| 2015/0256949 A1 | 9/2015 | Vanpoucke et al. |
| 2015/0264472 A1 | 9/2015 | Aase |
| 2015/0264501 A1 | 9/2015 | Hu et al. |
| 2015/0288944 A1* | 10/2015 | Nistico .................. G06T 15/20 345/156 |
| 2015/0317565 A1 | 11/2015 | Li et al. |
| 2015/0358751 A1 | 12/2015 | Deng et al. |

(56) References Cited

U.S. PATENT DOCUMENTS

| | | |
|---|---|---|
| 2015/0359436 A1 | 12/2015 | Shim et al. |
| 2015/0364058 A1 | 12/2015 | Lagree et al. |
| 2015/0373467 A1 | 12/2015 | Gelter |
| 2015/0373474 A1 | 12/2015 | Kraft et al. |
| 2015/0379251 A1 | 12/2015 | Komaki |
| 2016/0033280 A1 | 2/2016 | Moore et al. |
| 2016/0034249 A1 | 2/2016 | Lee et al. |
| 2016/0071526 A1 | 3/2016 | Wingate et al. |
| 2016/0072558 A1 | 3/2016 | Hirsch et al. |
| 2016/0073189 A1 | 3/2016 | Lindén et al. |
| 2016/0091980 A1* | 3/2016 | Baranski ............ G06F 1/163 345/156 |
| 2016/0094550 A1 | 3/2016 | Bradley et al. |
| 2016/0100262 A1 | 4/2016 | Inagaki |
| 2016/0119737 A1 | 4/2016 | Mehnert et al. |
| 2016/0124707 A1 | 5/2016 | Ermilov et al. |
| 2016/0125892 A1 | 5/2016 | Bowen et al. |
| 2016/0140870 A1 | 5/2016 | Connor |
| 2016/0142818 A1 | 5/2016 | Park |
| 2016/0162259 A1 | 6/2016 | Zhao et al. |
| 2016/0209691 A1 | 7/2016 | Yang et al. |
| 2016/0253994 A1 | 9/2016 | Panchapagesan et al. |
| 2016/0324478 A1 | 11/2016 | Goldstein |
| 2016/0353196 A1 | 12/2016 | Baker et al. |
| 2016/0360350 A1 | 12/2016 | Watson et al. |
| 2017/0021257 A1 | 1/2017 | Gilbert et al. |
| 2017/0046503 A1 | 2/2017 | Cho et al. |
| 2017/0059152 A1 | 3/2017 | Hirsch et al. |
| 2017/0060262 A1 | 3/2017 | Hviid et al. |
| 2017/0060269 A1 | 3/2017 | Förstner et al. |
| 2017/0061751 A1 | 3/2017 | Loermann et al. |
| 2017/0061817 A1 | 3/2017 | Mettler May |
| 2017/0062913 A1 | 3/2017 | Hirsch et al. |
| 2017/0064426 A1 | 3/2017 | Hviid |
| 2017/0064428 A1 | 3/2017 | Hirsch |
| 2017/0064432 A1* | 3/2017 | Hviid ............ H04R 1/1041 |
| 2017/0064437 A1 | 3/2017 | Hviid et al. |
| 2017/0078780 A1 | 3/2017 | Qian et al. |
| 2017/0078785 A1 | 3/2017 | Qian et al. |
| 2017/0100277 A1 | 4/2017 | Ke |
| 2017/0108918 A1 | 4/2017 | Boesen |
| 2017/0109131 A1 | 4/2017 | Boesen |
| 2017/0110124 A1 | 4/2017 | Boesen et al. |
| 2017/0110899 A1 | 4/2017 | Boesen |
| 2017/0111723 A1 | 4/2017 | Boesen |
| 2017/0111725 A1 | 4/2017 | Boesen et al. |
| 2017/0111726 A1 | 4/2017 | Martin et al. |
| 2017/0111740 A1 | 4/2017 | Hviid et al. |
| 2017/0112671 A1* | 4/2017 | Goldstein ............ A61B 5/0205 |
| 2017/0127168 A1 | 5/2017 | Briggs et al. |
| 2017/0131094 A1 | 5/2017 | Kulik |
| 2017/0142511 A1 | 5/2017 | Dennis |
| 2017/0146801 A1 | 5/2017 | Stempora |
| 2017/0150920 A1 | 6/2017 | Chang et al. |
| 2017/0151085 A1 | 6/2017 | Chang et al. |
| 2017/0151447 A1 | 6/2017 | Boesen |
| 2017/0151668 A1 | 6/2017 | Boesen |
| 2017/0151918 A1 | 6/2017 | Boesen |
| 2017/0151930 A1 | 6/2017 | Boesen |
| 2017/0151957 A1 | 6/2017 | Boesen |
| 2017/0151959 A1 | 6/2017 | Boesen |
| 2017/0153114 A1 | 6/2017 | Boesen |
| 2017/0153636 A1 | 6/2017 | Boesen |
| 2017/0154532 A1 | 6/2017 | Boesen |
| 2017/0155985 A1 | 6/2017 | Boesen |
| 2017/0155992 A1 | 6/2017 | Perianu et al. |
| 2017/0155993 A1 | 6/2017 | Boesen |
| 2017/0155997 A1 | 6/2017 | Boesen |
| 2017/0155998 A1 | 6/2017 | Boesen |
| 2017/0156000 A1 | 6/2017 | Boesen |
| 2017/0164890 A1 | 6/2017 | Leip et al. |
| 2017/0178631 A1 | 6/2017 | Boesen |
| 2017/0180842 A1 | 6/2017 | Boesen |
| 2017/0180843 A1 | 6/2017 | Perianu et al. |
| 2017/0180897 A1 | 6/2017 | Perianu |
| 2017/0188127 A1 | 6/2017 | Perianu et al. |
| 2017/0188132 A1 | 6/2017 | Hirsch et al. |
| 2017/0193978 A1 | 7/2017 | Goldman |
| 2017/0195829 A1 | 7/2017 | Belverato et al. |
| 2017/0208393 A1 | 7/2017 | Boesen |
| 2017/0214987 A1 | 7/2017 | Boesen |
| 2017/0215016 A1 | 7/2017 | Dohmen et al. |
| 2017/0230752 A1 | 8/2017 | Dohmen et al. |
| 2017/0251933 A1 | 9/2017 | Braun et al. |
| 2017/0257698 A1 | 9/2017 | Boesen et al. |
| 2017/0258329 A1 | 9/2017 | Marsh |
| 2017/0263236 A1 | 9/2017 | Boesen et al. |
| 2017/0263376 A1 | 9/2017 | Verschueren et al. |
| 2017/0266494 A1 | 9/2017 | Crankson et al. |
| 2017/0273622 A1 | 9/2017 | Boesen |
| 2017/0280257 A1 | 9/2017 | Gordon et al. |
| 2017/0301337 A1 | 10/2017 | Golani et al. |
| 2017/0361213 A1 | 12/2017 | Goslin et al. |
| 2017/0366233 A1 | 12/2017 | Hviid et al. |
| 2018/0007994 A1 | 1/2018 | Boesen et al. |
| 2018/0008194 A1 | 1/2018 | Boesen |
| 2018/0008198 A1 | 1/2018 | Kingscott |
| 2018/0009447 A1 | 1/2018 | Boesen et al. |
| 2018/0011006 A1 | 1/2018 | Kingscott |
| 2018/0011682 A1 | 1/2018 | Milevski et al. |
| 2018/0011994 A1 | 1/2018 | Boesen |
| 2018/0012228 A1 | 1/2018 | Milevski et al. |
| 2018/0013195 A1 | 1/2018 | Hviid et al. |
| 2018/0014102 A1 | 1/2018 | Hirsch et al. |
| 2018/0014103 A1 | 1/2018 | Martin et al. |
| 2018/0014104 A1 | 1/2018 | Boesen et al. |
| 2018/0014107 A1 | 1/2018 | Razouane et al. |
| 2018/0014108 A1 | 1/2018 | Dragicevic et al. |
| 2018/0014109 A1 | 1/2018 | Boesen |
| 2018/0014113 A1 | 1/2018 | Boesen |
| 2018/0014140 A1 | 1/2018 | Milevski et al. |
| 2018/0014436 A1 | 1/2018 | Milevski |
| 2018/0034951 A1 | 2/2018 | Boesen |
| 2018/0040093 A1 | 2/2018 | Boesen |
| 2018/0042501 A1 | 2/2018 | Adi et al. |

FOREIGN PATENT DOCUMENTS

| | | |
|---|---|---|
| CN | 104837094 A | 8/2015 |
| EP | 1469659 A1 | 10/2004 |
| EP | 1017252 A3 | 5/2006 |
| EP | 2903186 A1 | 8/2015 |
| GB | 2074817 | 4/1981 |
| GB | 2508226 A | 5/2014 |
| JP | 06292195 | 10/1998 |
| WO | 2008103925 A1 | 8/2008 |
| WO | 2008113053 A1 | 9/2008 |
| WO | 2007034371 A3 | 11/2008 |
| WO | 2011001433 A2 | 1/2011 |
| WO | 2012071127 A1 | 5/2012 |
| WO | 2013134956 A1 | 9/2013 |
| WO | 2014046602 A1 | 3/2014 |
| WO | 2014043179 A3 | 7/2014 |
| WO | 2015061633 A2 | 4/2015 |
| WO | 2015110577 A1 | 7/2015 |
| WO | 2015110587 A1 | 7/2015 |
| WO | 2016032990 A1 | 3/2016 |
| WO | 2016187869 A1 | 12/2016 |

OTHER PUBLICATIONS

Kuutti et al.: "Evaluation of a Doppler radar sensor system for vitals signs detection and activity monitoring in a radio-frequency shielded room", Measurement 68 (2015), 135-142, Journal homepage: www.elsevier.com/locate/measurement.

Madsen et al., "Signal Processing Methods for Doppler Radar Heart Rate Monitoring", US National Science Foundation, 21 pages, 2008.

Pittella: "Breath Activity Monitoring with Wearable UWB Radars: Measurement and Analysis of the Pulses Reflected by the Human Body", Article in IEEE Transactions on Biomedical Engineering,

(56) References Cited

OTHER PUBLICATIONS

Jul. 2016, 10pages, http://www.researchgate.net/publication/283513226.
Wang et al.: "Chest-Worn Health Monitor Based on a Bistatic Self-Injection-Locked Radar", 2015, 4 pages, Department of Electrical Engineering, National Sun Yat-Sen University, Taiwan.
Wang et al.: "Single-Antenna Doppler Radars Using Self and Mutual Injection Locking for Vital Sign Detection", IEEE, vol. 59, No. 12, Dec. 2011, pp. 3577-3587.
Wang et al.: "Wrist Pulse Rate Monitor Using Self-Injection-Locked Radar Technology", Biosensors 2016, 12 pages.
Stretchgoal—The Carrying Case for the Dash (Feb. 12, 2014).
Stretchgoal—Windows Phone Support (Feb. 17, 2014).
The Dash + The Charging Case & The BRAGI News (Feb. 21, 2014).
The Dash—A Word From Our Software, Mechanical and Acoustics Team + An Update (Mar. 11, 2014).
Update From BRAGI—$3,000,000—Yipee (Mar. 22, 2014).
Weisiger; "Conjugated Hyperbilirubinemia", Jan. 5, 2016.
Wertzner et al., "Analysis of fundamental frequency, jitter, shimmer and vocal intensity in children with phonological disorders", V. 71, n.5, 582-588, Sep./Oct. 2005; Brazilian Journal of Othrhinolaryngology.
Wikipedia, "Gamebook", https://en.wikipedia.org/wiki/Gamebook, Sep. 3, 2017, 5 pages.
Wikipedia, "Kinect", "https://en.wikipedia.org/wiki/Kinect", 18 pages, (Sep. 9, 2017).
Wikipedia, "Wii Balance Board", "https://en.wikipedia.org/wik/Wii_Balance_Board", 3 pages, (Jul. 20, 2017).
Akkermans, "Acoustic Ear Recognition for Person Identification", Automatic Identification Advanced Technologies, 2005 pp. 219-223.
Alzahrani et al: "A Multi-Channel Opto-Electronic Sensor to Accurately Monitor Heart Rate against Motion Artefact during Exercise", Sensors, vol. 15, No. 10, Oct. 12, 2015, pp. 25681-25702, XPO55334602, DOI: 10.3390/s151025681 the whole document.
Announcing the $3,333,333 Stretch Goal (Feb. 24, 2014).
Ben Coxworth: "Graphene-based ink could enable low-cost, foldable electronics", "Journal of Physical Chemistry Letters", Northwestern University, (May 22, 2013).
Blain: "World's first graphene speaker already superior to Sennheiser MX400", htt://www.gizmag.com/graphene-speaker-beats-sennheiser-mx400/31660, (Apr. 15, 2014).
BMW, "BMW introduces BMW Connected—The personalized digital assistant", "http://bmwblog.com/2016/01/05/bmw-introduces-bmw-connected-the-personalized-digital-assistant", (Jan. 5, 2016).
BRAGI Is on Facebook (2014).
BRAGI Update—Arrival of Prototype Chassis Parts—More People—Awesomeness (May 13, 2014).
BRAGI Update—Chinese New Year, Design Verification, Charging Case, More People, Timeline(Mar. 6, 2015).
BRAGI Update—First Sleeves From Prototype Tool—Software Development Kit (Jun. 5, 2014).
BRAGI Update—Let's Get Ready to Rumble, A Lot to Be Done Over Christmas (Dec. 22, 2014).
BRAGI Update—Memories From April—Update on Progress (Sep. 16, 2014).
BRAGI Update—Memories from May—Update on Progress—Sweet (Oct. 13, 2014).
BRAGI Update—Memories From One Month Before Kickstarter—Update on Progress (Jul. 10, 2014).
BRAGI Update—Memories From the First Month of Kickstarter—Update on Progress (Aug. 1, 2014).
BRAGI Update—Memories From the Second Month of Kickstarter—Update on Progress (Aug. 22, 2014).
BRAGI Update—New People @BRAGI—Prototypes (Jun. 26, 2014).
BRAGI Update—Office Tour, Tour to China, Tour to CES (Dec. 11, 2014).
BRAGI Update—Status on Wireless, Bits and Pieces, Testing—Oh Yeah, Timeline(Apr. 24, 2015).
BRAGI Update—The App Preview, The Charger, The SDK, BRAGI Funding and Chinese New Year (Feb. 11, 2015).
BRAGI Update—What We Did Over Christmas, Las Vegas & CES (Jan. 19, 2014).
BRAGI Update—Years of Development, Moments of Utter Joy and Finishing What We Started(Jun. 5, 2015).
BRAGI Update—Alpha 5 and Back to China, Backer Day, On Track(May 16, 2015).
BRAGI Update—Beta2 Production and Factory Line(Aug. 20, 2015).
BRAGI Update—Certifications, Production, Ramping Up (Nov. 13, 2015).
BRAGI Update—Developer Units Shipping and Status(Oct. 5, 2015).
BRAGI Update—Developer Units Started Shipping and Status (Oct. 19, 2015).
BRAGI Update—Developer Units, Investment, Story and Status(Nov. 2, 2015).
BRAGI Update—Getting Close(Aug. 6, 2015).
BRAGI Update—On Track, Design Verification, How It Works and What's Next(Jul. 15, 2015).
BRAGI Update—On Track, On Track and Gems Overview (Jun. 24, 2015).
BRAGI Update—Status on Wireless, Supply, Timeline and Open House@BRAGI(Apr. 1, 2015).
BRAGI Update-Unpacking Video, Reviews on Audio Perform and Boy Are We Getting Close(Sep. 10, 2015).
Healthcare Risk Management Review, "Nuance updates computer-assisted physician documentation solution" (Oct. 20, 2016).
Hoffman, "How to Use Android Beam to Wirelessly Transfer Content Between Devices", (Feb. 22, 2013).
Hoyt et. al., "Lessons Learned from Implementation of Voice Recognition for Documentation in the Military Electronic Health Record System", The American Health Information Management Association (2017).
Hyundai Motor America, "Hyundai Motor Company Introduces a Health + Mobility Concept for Wellness in Mobility", Fountain Valley, Californa (2017).
International Search Report & Written Opinion, PCT/EP16/70245 (dated Nov. 16, 2016).
International Search Report & Written Opinion, PCT/EP2016/070231 (dated Nov. 18, 2016).
International Search Report & Written Opinion, PCT/EP2016/070247 (dated Nov. 18, 2016).
International Search Report & Written Opinion, PCT/EP2016/07216 (dated Oct. 18, 2016).
International Search Report and Written Opinion, PCT/EP2016/070228 (dated Jan. 9, 2017).
Jain A et al: "Score normalization in multimodal biometric systems", Pattern Recognition, Elsevier, GB, vol. 38, No. 12, Dec. 31, 2005, pp. 2270-2285, XP027610849, ISSN: 0031-3203.
Last Push Before the Kickstarter Campaign Ends on Monday 4pm CET (Mar. 28, 2014).
Lovejoy: "Touch ID built into iPhone display one step closer as third-party company announces new tech", "http://9to5mac.com/2015/07/21/virtualhomebutton/" (Jul. 21, 2015).
Nemanja Paunovic et al, "A methodology for testing complex professional electronic systems", Serbian Journal of Electrical Engineering, vol. 9, No. 1, Feb. 1, 2012, pp. 71-80, XPO55317584, YU.
Nigel Whitfield: "Fake tape detectors, 'from the stands' footie and UGH? Internet of Things in my set-top box"; http://www.theregister.co.uk/2014/09/24/ibc_round_up_object_audio_dlna_iot/ (Sep. 24, 2014).
Nuance, "ING Netherlands Launches Voice Biometrics Payment System in the Mobile Banking App Powered by Nuance", "https://www.nuance.com/about-us/newsroom/press-releases/ing-netherlands-launches-nuance-voice-biometirics.html", 4 pages (Jul. 28, 2015).

(56) References Cited

OTHER PUBLICATIONS

Staab, Wayne J., et al., "A One-Size Disposable Hearing Aid is Introduced", The Hearing Journal 53(4):36-41) Apr. 2000.
Stretchgoal—It's Your Dash (Feb. 14, 2014).

* cited by examiner

USE OF BODY-WORN RADAR FOR BIOMETRIC MEASUREMENTS, CONTEXTUAL AWARENESS AND IDENTIFICATION

PRIORITY STATEMENT

This application claims priority to U.S. Provisional Patent Application No. 62/516,476, filed Jun. 7, 2017, entitled "Use of body-worn radar for biometric measurements, contextual awareness and identification" and hereby incorporated by reference in its entirety.

FIELD OF THE INVENTION

The present invention relates to wearable devices. More particularly, but not exclusively, the present invention relates to wireless earpieces.

BACKGROUND

Wearable devices including wireless earpieces or hearables hold great promise. What is needed are new and improved wearable devices that provide meaningful additional functionality and features which benefit users.

SUMMARY

Therefore, it is a primary object, feature, or advantage to improve over the state of the art.

It is a further object, feature, or advantage to provide a wireless earpiece or a set of wireless earpieces with enhanced functionality.

It is a still further object, feature, or advantage to provide a wireless earpiece or a set of wireless earpieces which provide meaningful benefits to users.

Another object, feature, or advantage is to provide a wireless earpiece or a set of wireless earpieces which provide for biometric measurements of a user.

Yet another object, feature, or advantage is to provide a wireless earpiece or a set of wireless earpieces which provide contextual awareness.

A further object, feature, or advantage is to provide a wireless earpiece of a set of wireless earpieces which provide for identification of a user.

One or more of these and/or other objects, features, or advantages will become apparent from the present application. No single embodiment need provide each and every object, feature, or advantage as different embodiments may have different objects, features, or advantages. Therefore, the present invention is not to be limited by or to these objects, features, or advantages.

According to one aspect, a method for utilizing radar from wireless earpieces includes steps of activating one or more radar sensors of the wireless earpieces, performing radar measurements of a user using the one or more radar sensors of the wireless earpieces, and analyzing the radar measurements to determine pulsatile measurements associated with the user, the analyzing performed using a processor of the wireless earpieces. The one or more radar sensors are internally focused on an ear of the user. The one or more radar sensors may be encompassed by a housing or frame of the wireless earpieces. The one or more radar sensors include a first set of sensors that are internally focused toward the user and a second set of sensors that are externally focused away from the user. The method may further include comparing a baseline radar signature of the user with a radar signature read by the one or more radar sensors to identify the user.

According to another aspect, a wireless earpiece is provided. The wireless earpiece may include an earpiece housing for fitting in an ear of a user, a processor controlling functionality of the wireless earpiece, a plurality of sensors to perform sensor measurements of the user, wherein the plurality of sensors include one or more radar sensors, and a transceiver capable of communicating with at least a wireless device. The processor may activate the one or more radar sensors to perform radar measurements, and analyze the radar measurements to determine pulsatile measurements associated with the user. The one or more radar sensors may include internally and externally facing radar sensors. The processor may compare a baseline radar signature of the user with a radar signature read by the one or more radar sensors to identify the user. The pulsatile measurements may include one or more of heart rate, heart rate variability, blood flow velocity, blood pressure, and respiration rate. The processor may isolate a Doppler frequency of a blood flow velocity from a composite signal represented by the radar measurements. The processor may determine the motion of the wireless earpiece, and positioning of the wireless earpiece relative to a head of the user.

According to another aspect, a wireless earpiece includes an earpiece housing adapted to fit into an ear of a user, a processor for executing a set of instructions, the processor disposed within the earpiece housing, at least one radar sensor operatively connected to the processor, and a memory operatively connected to the processor for storing the set of instructions, wherein the instructions are executed to activate one or more of the at least one radar sensors of the wireless earpieces, perform radar measurements of the user, and analyze the radar measurements to determine pulsatile measurements associated with the user.

DETAILED DESCRIPTION

Figure 1:
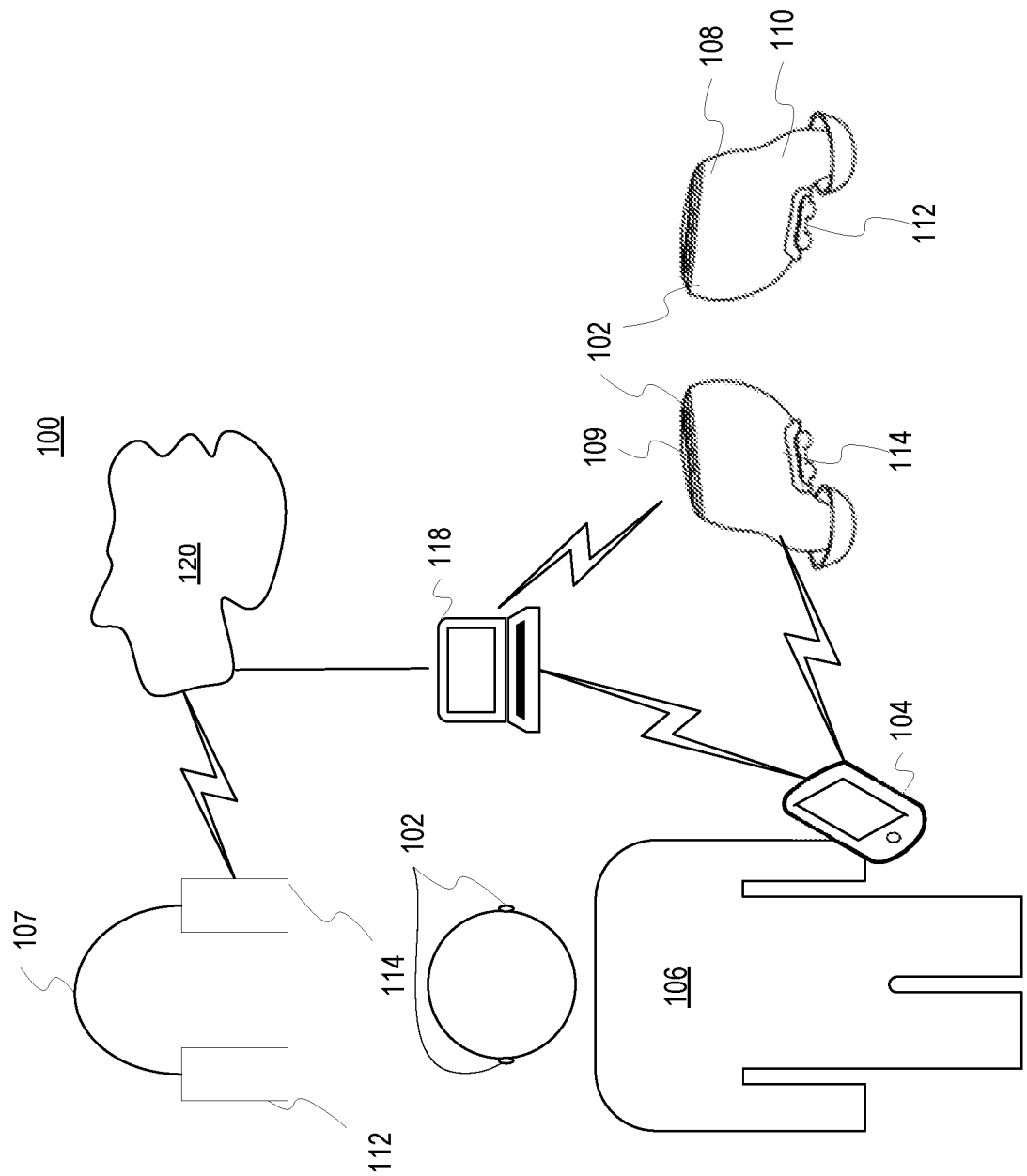
FIG. 1 is a pictorial representation of a communication system.

The illustrative embodiments provide a system, method, and wireless earpieces for utilizing radar to detect user biometrics, identifying the user, and providing contextual awareness. In one embodiment, the wireless earpieces may be worn to provide media content to a user and may also capture user biometrics utilizing any number of sensors. The sensors may include a radar sensor that may be utilized to detect biometrics, such as heart rate, blood pressure, blood oxygenation, heart rate variability, blood velocity, and so forth. The radar sensor may also detect the orientation, location, motion, and distances of the wireless earpieces as well as the wireless earpieces relative to other electronic devices (e.g., paired, linked, communicating devices, etc.). The wireless earpieces may represent any number of shapes and configurations, such as wireless earbuds or a wireless headset.

The radar sensor may be configured as an active, passive, or combination sensor. In various embodiments, the radar sensor may be internally or externally focused. For example, internally focused radar sensors may perform any number of measurements, readings, or functions including, but not limited to, measuring/tracking the motion and orientation of a user or other target/body (e.g., translational, rotational displacement, velocity, acceleration, etc.), determining material properties of a target/body (e.g., glass, steel, wood, density, etc.), and determining a physical structure of a target/body (e.g., layer analysis, depth measurements, material composition, external and internal shape, construction of an object, etc.). The specific measurements of the wireless earpieces may be focused on user biometrics, such as heart rate, blood flow velocity, status of the wireless earpieces (e.g., worn, in storage, positioned on a desk, etc.), identification of the user, and so forth. The utilization of radar in the wireless earpieces may be beneficial because of insensitivity to ambient light, skin pigmentation, and because direct sensor-user contact is not required. The utilization of radar sensors may also allow the sensors to be completely encapsulated, enclosed, or otherwise integrated in the wireless earpieces shielding the radar sensors from exposure to sweat/fluids, water, dirt, and dust.

The illustrative embodiments may utilize the Doppler frequency of the blood flow velocity determined from a composite signal detected by the sensors of the wireless earpieces. Utilization of radar sensors may provide for more reliable detection of whether the wireless earpieces are being worn in the ears of the user. The wireless earpieces may also self-determine a location, such as in a pocket, on a desk, in a hand, in a bag, in a smart charger, within a container, or so forth. The location determined by the radar sensors may also be synchronized with a wireless device in the event the user forgets or misplaces the wireless earpieces so that a record of the last known position or estimated position is recorded.

The illustrative embodiments may also determine whether the user is an authorized user utilizing a radar signature determined by the radar sensors. For example, the radar sensors may determine the size and shape of the users inner and outer ear as well as other facial structures, such as cheek shape, jaw bone and muscle arrangements, and so forth. In addition, the wireless earpieces may be utilized alone or as a set. When utilized as a set, the signals or determinations may be combined to determine information, such as the orientation of the left wireless earpiece and the right wireless earpiece relative to one another and the user's head, distance between the wireless earpieces, motion of the wireless earpieces relative to one another and the user's head, and so forth. In one embodiment, the radar measurements may measure physiological parameters from which a pulsatile component (e.g., heart rate) may be determined.

The illustrative embodiments may also be applicable to any number of other wearable devices, systems, or components, such as smart watches, headsets, electronic clothing/shoes, anklets, or so forth. As noted, both internally facing (toward the user) and externally facing radar sensors may be utilized. The wireless earpieces may communicate with any number of communications or computing devices (e.g., cell phones, smart helmets, vehicles, emergency beacons, smart clothing, emergency service personnel, designated contacts, etc.).

The radar sensors may utilize continuous wave and pulsed wave communications (active detection) as well as ambient environmental signals, such as Wi-Fi, Bluetooth, and so forth. For example, a Doppler signal may be utilized to detect a heart rate based on detected motion (e.g., rotation, displacement, deformation, acceleration, fluid-flow velocity, vortex shedding Poiseuille's law, Navier Stoke's equations, etc.).

FIG. 1 is a pictorial representation of a communications environment 100 in accordance with an illustrative embodiment. The wireless earpieces 102 may be configured to communicate with each other and with one or more wireless devices, such as a wireless device 104 or a personal computer 118. The wireless earpieces 102 may be worn by a user 106 and are shown both as worn and separately from their positioning within the ears of the user 106 for purposes of visualization. A block diagram of the wireless earpieces 102 if further shown in FIG. 4 to further illustrate components and operation of the wireless earpieces 102 including the radar systems or components. The wireless earpieces 102 may be shaped and configured as wireless earbuds, wireless headphones 107, or other headpieces, personal speaker/communications devices, or earpieces any of which may be referred to generally as wireless earpieces 102.

The headphones 107 may include sensors that are not within the ear canal. The headphones 107 may include sensors that are integrated with an over-head support, ear pads/cups, a frame, or so forth. The biometrics may be measured from the user's head (e.g., ears, neck, ears, scalp, skin, etc.) or body. The information may also be associated with the environment, user activity/actions, ambient, or so forth.

In one embodiment, the wireless earpieces 102 includes a housing or frame 108 shaped to fit substantially within the ears of the user 106. The housing or frame 108 is a support structure that at least partially encloses and houses the electronic components of the wireless earpieces 102. The frame 108 may be composed of a single structure (e.g., plastic or composite molding) or multiple structures that are interconnected. The frame 108 protects the components of the wireless earpieces 102 and may flex or deform slightly when dropped on or stepped on to protect the internal components. An exterior portion of the wireless earpieces 102 may include a first set of sensors shown as infrared sensors 109. The infrared sensors 109 may include emitter and receivers that detects and measures infrared light radiating from objects in its field of view. The infrared sensors 109 may detect gestures, touches, or other user input against an exterior portion of the wireless earpieces 102 that is visible when worn by the user 106. The infrared sensors 109 may also detect infrared light or motion. The infrared sensors 109 may be utilized to determine whether the wireless earpieces 102 are being worn, moved, approached by a user, set aside, stored in a smart case, placed in a dark environment, or so forth.

The frame 108 defines an extension 110 configured to fit substantially within the ear of the user 106. The extension 110 may include one or more speakers or vibration components for interacting with the user 106. All or portions of the extension 110 may be removable covered by one or more sleeves. The sleeves may be changed to fit the size and shape of the user's ears. The sleeves may come in various sizes and have extremely tight tolerances to fit the user 106 and one or more other users that may utilize the wireless earpieces 102 during their expected lifecycle. In another embodiment, the sleeves may be custom built to support the interference fit utilized by the wireless earpieces 102 while also being comfortable while worn. The sleeves are shaped and configured to not cover various sensor devices of the wireless earpieces 102.

In one embodiment, the frame 108 or the extension 110 (or other portions of the wireless earpieces 102) may include sensors 112 for sensing heart rate, blood oxygenation, temperature, heart rate variability, blood velocity, voice characteristics, skin conduction, glucose levels, impacts, activity level, position, motion, particulates, chemical content, location, orientation, as well as any number of internal or external user biometrics. The sensors 112 may be partially or completely encompassed or integrated with the frame 108 or the extension 110. In other embodiments, the sensors 112 may be positioned to contact or be proximate the epithelium of the external auditory canal or auricular region of the user's ears when worn. For example, the sensors 112 may represent various metallic sensor contacts, optical interfaces, radar, or even micro-delivery systems for receiving, measuring, and delivering information and signals. Small electrical charges, the Doppler effect, or spectroscopy emissions (e.g., various light wavelengths) may be utilized by the sensors 112 to analyze the biometrics of the user 106 including pulse, blood pressure, skin conductivity, blood analysis, sweat levels, and so forth. In one embodiment, the sensors 112 may include optical sensors that may emit and measure reflected light within the ears of the user 106 to measure any number of biometrics. The optical sensors may also be utilized as a second set of sensors to determine when the wireless earpieces 102 are in use, stored, charging, or otherwise positioned.

In one embodiment, the sensors 112 may include a radar sensor 114 (the sensors 112 and the radar sensor 114 may also be included in the headphone 107). The radar sensor 114 may be at least partially enclosed or encompassed within a housing or frame 108. The radar sensor 114 may detect gestures or micro gestures performed by the user. In another embodiment, the radar sensor 114 may be a separate sensing component proximate the sensors 112 or positioned at one or more locations proximate the skin or tissue of the user. The radar sensor 114 may utilize any number of radar signals, bands, waves, or technologies (e.g., Google's Developing Project Soli). For example, the radar sensor 114 may operate at approximately 60 GHz and scanning at 10 frames per second. In some embodiments, the signal frequency/band (e.g., IEEE HF, VHF, UHF, L, S, C, X K, Ku, Ka, mm, V, W, F, D, G, Y, J, etc.), scanning interval, and other variables may be automatically configured, manually set, or set based on application. For example, the radar sensor 114 may include Hz, kHz, MHz, GHz, millimeter-wave, and/or terahertz radar systems. The radar sensor 114 may implement an important role in multimodal layered sensing systems targeted at measuring both physiological and behavioral biometric data. The illustrative embodiments may utilize the radar sensor 114 to detect blood pressure, heart rate variability, blood velocity, user identification, and so forth. The radar sensor 114 of both the left wireless earpiece and the right wireless earpiece may work in combination to ensure accurate readings are performed. The wireless earpieces 102 may utilize mathematic, error correction, and measurement processes, such as averaging, sampling, medians, thresholds, or so forth to ensure that all measurements by the radar sensors 113 are accurate. The radar sensor 114 may include logic, memory, transmitters, receivers, antennas (e.g., two or more), amplifiers, circuits, filters, interfaces, ports, connectors and so forth.

The sensors 112 may be utilized to provide relevant information that may be communicated through the wireless earpieces 102. As described, the sensors 112 may include one or more microphones that may be integrated with the frame 108 or the extension of the wireless earpieces 102. For example, an external microphone may sense environmental noises as well as the user's voice as communicated through the air of the communications environment 100. An ear-bone or internal microphone may sense vibrations or sound waves communicated through the head of the user 102 (e.g., bone conduction, etc.).

In some applications, temporary adhesives or securing mechanisms (e.g., clamps, straps, lanyards, extenders, etc.) may be utilized to ensure that the wireless earpieces 102 remain in the ears of the user 106 even during the most rigorous and physical activities or to ensure that if they do fall out, the wireless earpieces 102 are not lost or broken. For example, the wireless earpieces 102 may be utilized during marathons, swimming, team sports, biking, hiking, parachuting, or so forth. In one embodiment, miniature straps may attach to the wireless earpieces 102 with a clip on the strap securing the wireless earpieces to the clothes, hair, or body of the user. The wireless earpieces 102 may be configured to play music or audio, receive and make phone calls or other communications, determine ambient environmental conditions (e.g., temperature, altitude, location, speed, heading, etc.), read user biometrics (e.g., heart rate, motion, temperature, sleep, blood oxygenation, voice output, calories burned, forces experienced, etc.), and receive user input, feedback, or instructions. The wireless earpieces 102 may also execute any number of applications to perform specific purposes. The wireless earpieces 102 may be utilized with any number of automatic assistants, such as Siri, Cortana, Alexa, Google, Watson, or other smart assistants/artificial intelligence systems.

The communications environment 100 may further include the personal computer 118. The personal computer 118 may communicate with one or more wired or wireless networks, such as a network 120. The personal computer 118 may represent any number of devices, systems, equipment, or components, such as a laptop, server, tablet, medical system, gaming device, virtual/augmented reality system, or so forth. The personal computer 118 may communicate utilizing any number of standards, protocols, or processes. For example, the personal computer 118 may utilize a wired or wireless connection to communicate with the wireless earpieces 102, the wireless device 104, or other electronic devices. The personal computer 118 may utilize any number of memories or databases to store or synchronize biometric information associated with the user 106, data, passwords, or media content.

The wireless earpieces 102 may determine their position with respect to each other as well as the wireless device 104 and the personal computer 118. The components of the sensors 112 as well as the sensors of the wireless device 104 and the personal computer may be utilized to determine relative position, orientation, motion, and so forth. For example, position information for the wireless earpieces 102 and the wireless device 104 may determine proximity of the devices in the communications environment 100. For example, global positioning information, radar measurements, or signal strength/activity may be utilized to determine proximity and distance of the devices to each other in the communications environment 100. In one embodiment, the distance information may be utilized to determine whether biometric analysis may be displayed to a user. For example, the wireless earpieces 102 may be required to be within four feet of the wireless device 104 and the personal computer 118 in order to display biometric readings or receive user input. The transmission power or amplification of received signals may also be varied based on the proximity of the devices in the communications environment 100.

In one embodiment, the wireless earpieces 102 and the corresponding sensors 112 (whether internal or external) may be configured to take a number of measurements or log information and activities during normal usage. This information, data, values, and determinations may be reported to the user or otherwise utilized as part of the virtual assistant. The sensor measurements may be utilized to extrapolate other measurements, factors, or conditions applicable to the user 106 or the communications environment 100. For example, the sensors 112 may monitor the user's usage patterns or light sensed in the communications environment 100 to enter a full power mode in a timely manner. The user 106 or another party may configure the wireless earpieces 102 directly or through a connected device and application (e.g., mobile app with a graphical user interface) to set power settings (e.g., preferences, conditions, parameters, settings, factors, etc.) or to store or share biometric information, audio, and other data. In one embodiment, the user may establish the light conditions or motion that may activate the full power mode or that may keep the wireless earpieces 102 in a sleep or low power mode. As a result, the user 106 may configure the wireless earpieces 102 to maximize the battery life based on motion, lighting conditions, and other factors established for the user. For example, the user 106 may set the wireless earpieces 102 to enter a full power mode only if positioned within the ears of the user 106 within ten seconds of being moved, otherwise the wireless earpieces 102 remain in a low power mode to preserve battery life. This setting may be particularly useful if the wireless earpieces 102 are periodically moved or jostled without being inserted into the ears of the user 106. Any of the sensors 112 including the radar sensor 114 may be utilized to perform the respective determinations.

The user 106 or another party may also utilize the wireless device 104 to associate user information and conditions with the user preferences. For example, an application executed by the wireless device 104 may be utilized to specify the conditions (e.g., user biometrics read by the sensors 112) that may "wake up" the wireless earpieces 102 to automatically or manually communicate information, warnings, data, or status information to the user. Initial readings may also be recorded by the sensors 112 to create an identification and authorization profile including data, information, and measurements. The measurements may include voice analysis, height analysis, skin reflectivity, skin conductivity, radar profile, optical profile, and so forth. For example, the radar sensor 114 may be utilized to create a radar profile of the user's ear/head for automatically identifying the user when wearing the wireless earpieces 102. In addition, the enabled functions or components (e.g., sensors, transceivers, vibration alerts, speakers, lights, etc.) may be selectively activated based on the user preferences as set by default, by the user, or based on historical information. In another embodiment, the wireless earpieces 102 may be adjusted or trained over time to become even more accurate in adjusting to authentication information, habits, requirements, requests, activations, or other processes or functions performed by the wireless earpieces 102 for the user (e.g., applications, virtual assistants, etc.).

The wireless earpieces 102 may utilize historical information to generate default values, baselines, thresholds, policies, or settings for determining when and how various communications, actions, and processes are implemented. As a result, the wireless earpieces 102 may effectively manage the automatic and manually performed processes of the wireless earpieces 102 based on automatic detection of events and conditions (e.g., light, motion, user sensor readings, etc.) and user specified settings. For example, the authorization information may be utilized to subsequently identify the user and perform authentication.

As previously noted, the wireless earpieces 102 may include any number of sensors 112 and logic for measuring and determining user biometrics, such as pulse rate, skin conduction, blood oxygenation, blood velocity, skin/tissue/organ displacement, blood pressure, heart rate variability, blood velocity, temperature, calories expended, blood or excretion chemistry, voice and audio output, position, and orientation (e.g., body, head, etc.). The sensors 112 may also determine the user's location, position, velocity, impact levels, and so forth. Any of the sensors 112 may be utilized to detect or confirm light, motion, or other parameters that may affect how the wireless earpieces 102 manage, utilize, and initialize various processes, components, and functions. The sensors 112 may also receive user input and convert the user input into commands or selections made across the personal devices of the personal area network. For example, the user input detected by the wireless earpieces 102 may include voice commands, head motions, finger taps, finger swipes, motions or gestures, or other user inputs sensed by the wireless earpieces. The user input may be determined by the wireless earpieces 102 and converted into authorization commands that may be sent to one or more external devices, such as the wireless device 104, the personal computer 118, a tablet computer, or so forth. For example, the user 106 may create a specific head motion and voice command that when detected by the wireless earpieces 102 are utilized to send a request (implemented by the wireless earpiece or wireless earpieces 102/wireless device 104) to provide the user information or options, such as her current heart rate, speed, approaching objects, and location. In another example, the sensors 112 may prepare the wireless earpieces 102 for an impact in response to determining the wireless earpieces 102 are free falling or have been dropped (e.g., device power down, actuator compression/shielding of sensitive components, etc.).

The sensors 112 may make all of the measurements with regard to the user 106 and communications environment 100 or may communicate with any number of other sensory devices, components, or systems in the communications environment 100. In one embodiment, the communications environment 100 may represent all or a portion of a personal area network. The wireless earpieces 102 may be utilized to control, communicate, manage, or interact with a number of other wearable devices or electronics, such as smart glasses, helmets, smart glass, watches or wrist bands, other wireless earpieces, chest straps, implants, displays, clothing, or so forth. A personal area network is a network for data transmissions among devices, components, equipment, and systems, such as personal computers, communications devices, cameras, vehicles, entertainment/media devices, and medical devices. The personal area network may utilize any number of wired, wireless, or hybrid configurations and may be stationary or dynamic. For example, the personal area network may utilize wireless network protocols or standards, such as INSTEON, IrDA, Wireless USB, Bluetooth, Z-Wave, ZigBee, Wi-Fi, ANT+ or other applicable radio frequency signals. In one embodiment, the personal area network may move with the user 106.

In other embodiments, the communications environment 100 may include any number of devices, components, or so forth that may communicate with each other directly or indirectly through a wireless (or wired) connection, signal, or link. The communications environment 100 may include one or more networks and network components and devices represented by the network 120, such as routers, servers, signal extenders, intelligent network devices, computing devices, or so forth. In one embodiment, the network 120 of the communications environment 100 represents a personal area network as previously disclosed.

Communications within the communications environment 100 may occur through the network 120 or may occur directly between devices, such as the wireless earpieces 102 and the wireless device 104. The network 120 may communicate with or include a wireless network, such as a Wi-Fi, cellular (e.g., 3G, 4G, 5G, PCS, GSM, etc.), Bluetooth, or other short range or long range radio frequency networks, signals, connections, or links. The network 120 may also include or communicate with any number of hard wired networks, such as local area networks, coaxial networks, fiber-optic networks, network adapters, or so forth. Communications within the communications environment 100 may be operated by one or more users, service providers, or network providers.

The wireless earpieces 102 may play, display, communicate, or utilize any number of alerts or communications to indicate that the actions, activities, communications, mode, or status in use or being implemented. For example, one or more alerts may indicate when various processes are implemented automatically or manually selected by the user. The alerts may indicate when actions are in process, authorized, and/or changing with specific tones, verbal acknowledgements, tactile feedback, or other forms of communicated messages. For example, an audible alert and LED flash may be utilized each time the wireless earpieces 102 receive user input. Verbal or audio acknowledgements, answers, and actions utilized by the wireless earpieces 102 are effective because of user familiarity with such devices in standard smart phone and personal computers. The corresponding alert may also be communicated to the user 106, the wireless device 104, and the personal computer 118.

In another embodiment, the wireless earpieces 102 may communicate a proximity, status change, location, or orientation alert based on the measurements performed by the sensors 112. For example, if the heart rate has changed significantly (e.g., dangerous thresholds exceeded—low or high), an alert may be sent to the user 106 or to one or more connected devices (e.g., wireless device 104, computer 118, etc.). In another example, an alert may be played in response to an approaching object. The alerts may be utilized with any number of other systems to protect or assist the user.

In other embodiments, the wireless earpieces 102 may also vibrate, flash, play a tone or other sound, or give other indications of the actions, status, or process implemented. The wireless earpieces 102 may also communicate an alert to the wireless device 104 that shows up as a notification, message, or other indicator indicating changes in status, actions, commands, or so forth. The type of alert may be specific to the indicated status, action, command or so forth. For example, user preferences may allow the user to specify how and when each alert is utilized.

The wireless earpieces 102 as well as the wireless device 104 may include logic for automatically implementing the virtual assistant in response to motion, light, user activities, user biometric status, user location, user position, historical activity/requests, or various other conditions and factors of the communications environment 100. The virtual assistant may be activated to perform a specified activity or to "listen" or be prepared to "receive" user input, feedback, or commands for implementation by the virtual assistant.

The wireless device 104 may represent any number of wireless or wired electronic communications or computing devices, such as smart phones, laptops, desktop computers, servers, entertainment systems, control systems, tablets, displays, gaming devices, music players, personal digital assistants, vehicle systems, or so forth. The wireless device 104 may communicate utilizing any number of wireless connections, standards, or protocols (e.g., near field communications, NFMI, Bluetooth, Wi-Fi, wireless Ethernet, etc.). For example, the wireless device 104 may be a touch screen cellular phone that communicates with the wireless earpieces 102 utilizing Bluetooth communications. The wireless device 104 may implement and utilize any number of operating systems, kernels, instructions, or applications that may make use of the available sensor data sent from the wireless earpieces 102. For example, the wireless device 104 may represent any number of android, iOS, Windows, open platforms, or other systems and devices. Similarly, the wireless device 104 or the wireless earpieces 102 may execute any number of applications that utilize the user input, proximity data, biometric data, and other feedback from the wireless earpieces 102 to initiate, authorize, or process virtual assistant processes and perform the associated tasks.

As noted, the layout of the internal components of the wireless earpieces 102 and the limited space available for a product of limited size may affect where the sensors 112 may be positioned. The positions of the sensors 112 within each of the wireless earpieces 102 may vary based on the model, version, and iteration of the wireless earpiece design and manufacturing process.

Figure 2:
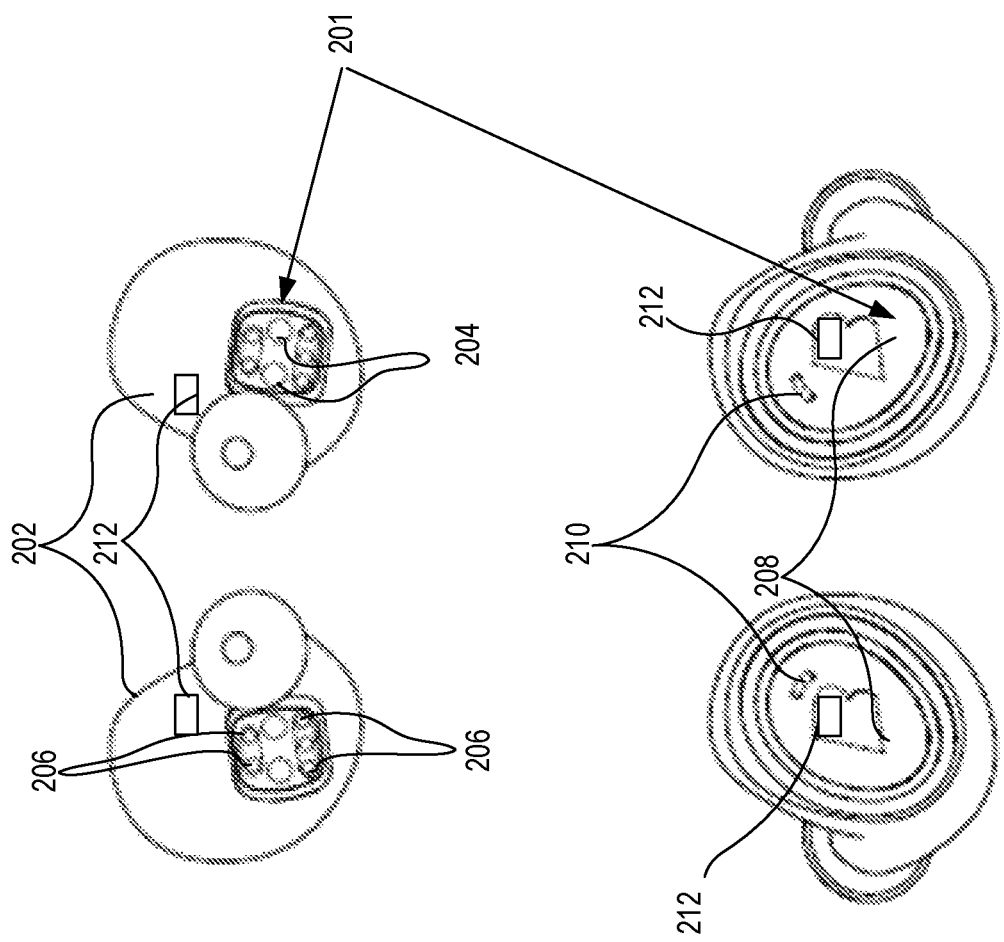
FIG. 2 is a pictorial representation of sensors of the wireless earpieces.

FIG. 2 is a pictorial representation of some of the sensors 201 of wireless earpieces 202 in accordance with illustrative embodiments. As previously noted, the wireless earpieces 202 may include any number of internal or external sensors. In one embodiment, the sensors 201 may be utilized to determine user biometrics, environmental information associated with the wireless earpieces 202, and use status of the wireless earpieces 202. Similarly, any number of other components or features of the wireless earpieces 202 may be managed based on the measurements made by the sensors 201 to preserve resources (e.g., battery life, processing power, etc.), gather additional information, and so forth. The sensors 201 may make independent measurements or combined measurements utilizing the sensory functionality of each of the sensors 201 to measure, confirm, or verify sensor measurements. For example, the wireless earpieces 202 may represent a set or pair of wireless earpieces or the left wireless earpiece and the right wireless earpiece that may operate independent of each other as situations may require.

In one embodiment, the sensors 201 may include optical sensors 204, contact sensors 206, infrared sensors 208, microphones 210, and radar sensors 212. The optical sensors 204 may generate an optical signal that is communicated to the ear (or other body part) of the user and reflected back. The reflected optical signal may be analyzed to determine blood pressure, pulse rate, pulse oximetry, vibrations, blood chemistry, and other information about the user. The optical sensors 204 may include any number of sources for outputting various wavelengths of electromagnetic radiation (e.g., infrared, laser, etc.) and visible light. Thus, the wireless earpieces 202 may utilize spectroscopy as it is known in the art and developing to determine any number of user biometrics.

The optical sensors 204 may also be configured to detect ambient light proximate the wireless earpieces 202. For example, the optical sensors 204 may detect light and light changes in an environment of the wireless earpieces 202, such as in a room where the wireless earpieces 202 are located (utilizing optical sensors 204 that are internally and externally positioned with regard to the body of the user). The optical sensors 204 may be configured to detect any number of wavelengths including visible light that may be relevant to light changes, approaching users or devices, and so forth.

In another embodiment, the optical sensors 204 may include any number of cameras. The cameras may be front facing, side facing, rear facing, fisheye, 360°, or so forth. The cameras may be utilized to determine proximity of other users, structures, objects, or so forth. The cameras may be equipped with facial, character, or object recognition for recognizing people, places, hand or body gestures, objects, or other applicable information. The measurements, images, or video captured by the optical sensors 204 may be processed, analyzed, queued, or saved for subsequent usage.

In another embodiment, the contact sensors 206 may be utilized to determine that the wireless earpieces 202 are positioned within the ears of the user. For example, conductivity of skin or tissue within the user's ear may be utilized to determine that the wireless earpieces are being worn. In other embodiments, the contact sensors 206 may include pressure switches, toggles, or other mechanical detection components for determining that the wireless earpieces 202 are being worn. The contact sensors 206 may measure or provide additional data points and analysis that may indicate the biometric information of the user. The contact sensors 206 may also be utilized to apply electrical, vibrational, motion, or other input, impulses, or signals to the skin of the user to detect utilization or positioning.

The wireless earpieces 202 may also include infrared sensors 208. The infrared sensors 208 may be utilized to detect touch, contact, gestures, or other user input. The infrared sensors 208 may detect infrared wavelengths and signals. In another embodiment, the infrared sensors 208 may detect visible light or other wavelengths as well. The infrared sensors 208 may be configured to detect light or motion or changes in light or motion. Readings from the infrared sensors 208 and the optical sensors 204 may be configured to detect light, gestures, or motion. The readings may be compared to verify or otherwise confirm light or motion. As a result, decisions regarding user input, biometric readings, environmental feedback, and other measurements may be effectively implemented in accordance with readings form the sensors 201 as well as other internal or external sensors and the user preferences. The infrared sensors 208 may also include touch sensors integrated with or proximate the infrared sensors 208 externally available to the user when the wireless earpieces 202 are worn by the user.

The wireless earpieces 202 may include microphones 210. The microphones 210 may represent external microphones as well as internal microphones. The external microphones may be positioned exterior to the body of the user as worn. The external microphones may sense verbal or audio input, feedback, and commands received from the user. The external microphones may also sense environmental, activity, additional users (e.g., clients, jury members, judges, attorneys, paramedics, etc.), and external noises and sounds. The internal microphone may represent an ear-bone or bone-conduction microphone. The internal microphone may sense vibrations, waves, or sound communicated through the bones and tissue of the user's body (e.g., skull). The microphones 210 may sense input, feedback, and content that is utilized by the wireless earpieces 202 to implement the processes, functions, and methods herein described. The audio input sensed by the microphones 210 may be filtered, amplified, or otherwise processed before or after being sent to the processor/logic of the wireless earpieces 202.

In one embodiment, the wireless earpieces 202 may include the radar sensors 212. The radar sensors 212 may include or utilize pulse radar, continuous wave radar, active, passive, laser, ambient electromagnetic field, or radio frequency radiation or signals or any number of other radar methodologies, systems, processes, or components. In one embodiment, the radar sensors 212 may utilize ultrasonic pulse probes that rely on the Doppler effect or ultra-wide band sensing to detect the relative motion of blow flow of the user from the wireless earpieces 202. In one embodiment, the physiological measurements performed by the radar sensors 212 may be limited to the ear of the user. In another embodiment, the radar sensors 212 may be able to measure other biometrics, such as heart motion, respiration, and so forth. For example, the radar sensors 212 may include a radar seismocardiogram (R-SCG) that utilizes radio frequency integrated circuits with the wireless earpieces 202 to measure user biometrics with small, low-power radar units. The radar sensors 212 may also be utilized to biometrically identify the user utilizing the structure, reflective properties, or configuration of the user's ear, head, and/or body (similar to utilization of fingerprints). For example, the radar sensors 212 may perform analysis to determine whether the user is an authorized or verified user.

In one embodiment, the radar sensors 212 may include one or more of a synchronizer, modulator, transmitter, duplexer, receiver, and other radar components. The transmitter and receiver may be at the same location (monostatic radar) within the wireless earpieces 202 or may be integrated at different locations (bistatic radar). The radar sensors 212 may be configured to utilize different carrier, pulse widths, pulse repetition frequencies, polarizations, filtering (e.g., matched filtering, clutter, signal-to-noise ratio), or so forth. In one embodiment, the radar sensors 212 may be integrated circuits or chips that performs Doppler based measurements of blood flow.

The radar sensor 212 may include inwardly facing and externally facing radar. For example, internally facing radar may be utilized to measure user biometrics. Externally facing radar may measure user information, environmental information, and other applicable information and data.

The illustrative embodiments may include some or all of the sensors 201 described herein. In one embodiment, the wireless earpieces 102 may include the radar sensors 212 without the optical sensors 204 and infrared sensors 208. In one embodiment, the radar sensors 212 may utilize the signals from transceivers already integrated into the wireless earpieces 102 to generate a signal and receive the corresponding reflection. The radar sensors 212 may also represent sonar or ultrasound sensors.

In another embodiment, the wireless earpieces 202 may include chemical sensors (not shown) that perform chemical analysis of the user's skin, excretions, blood, or any number of internal or external tissues or samples. For example, the chemical sensors may determine whether the wireless earpieces 202 are being worn by the user. The chemical sensor may also be utilized to monitor important biometrics that may be more effectively read utilizing chemical samples (e.g., sweat, blood, excretions, etc.). In one embodiment, the chemical sensors are non-invasive and may only perform chemical measurements and analysis based on the externally measured and detected factors. In other embodiments, one or more probes, vacuums, capillary action components, needles, or other micro-sampling components may be utilized. Minute amounts of blood or fluid may be analyzed to perform chemical analysis that may be reported to the user and others. The sensors 201 may include parts or components that may be periodically replaced or repaired to ensure accurate measurements. In one embodiment, the infrared sensors 208 may be a first sensor array and the optical sensors 204 may be a second sensor array.

Figure 3:
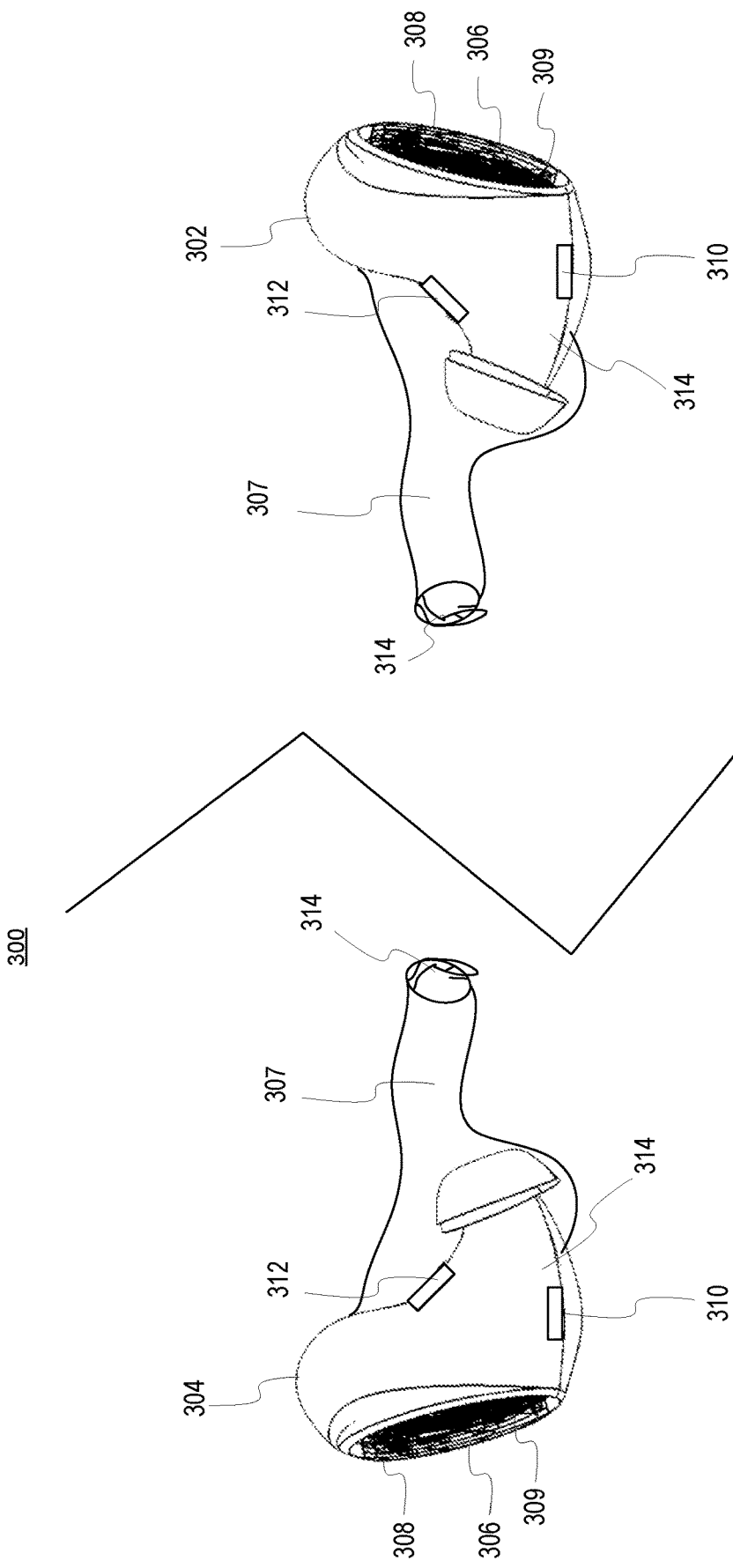
FIG. 3 is pictorial representation of a right wireless earpiece and a left wireless earpiece of a wireless earpiece set.

FIG. 3 is a pictorial representation of a right wireless earpiece 302 and a left wireless earpiece 304 of a wireless earpiece set 300 in accordance with an illustrative embodiment. For example, the right wireless earpiece 302 is shown as it relates to a user's or third party's right ear and the left wireless earpiece 304 is shown as it relates to a user's or third party's left ear. The user or third party may interact with the right wireless earpiece 302 or the left wireless earpiece 304 by either providing a gesture sensed by a gesture interface 306, a voice command sensed via a microphone 308, or by one or more head or neck motions which may be sensed by an inertial sensor 309, such as a MEMS gyroscope, magnetometer, or an electronic accelerometer.

In one embodiment, the gesture interface 306 may include one or more optical sensors, touch/capacitive sensors, or so forth. The microphone 308 may represent one or more over-air and/or bone conduction microphones. The air-based microphone may be positioned on an exterior of the right wireless earpiece 302 and left wireless earpiece 304 when worn by the user. The bone conduction microphone may be positioned on an interior portion of the right wireless earpiece 302 or the left wireless earpiece 304 to abut the skin, tissues, and bones of the user.

The wireless earpiece set 300 may include one or more radar sensors for each of the right wireless earpiece and the left wireless earpiece. In one embodiment (not shown), the right wireless earpiece 302 and the left wireless earpiece 304 may each include a single radar unit. As shown, the right wireless earpiece 302 and the left wireless earpiece 304 may each include a first radar unit 310 and a second radar unit 312. In one embodiment, the first radar unit 310 and the second radar unit 312 may be completely enclosed within a frame 314 of the right wireless earpiece 302 and the left wireless earpiece 304. In another embodiment, the first radar unit 310 and the second radar unit 312 may be positioned flush with an outer edge of the frame 314. In yet another embodiment, the first radar unit 310 and the second radar unit 312 may protrude slightly from an outer edge of the frame 314.

In one embodiment, the first radar unit 310 and the second radar unit 312 may be positioned adjacent or proximate each other within each of the wireless earpieces 304, 306. For example, the first radar unit 310 may transmit a signal and the second radar unit 312 may detect the reflections of the signal sent from the first radar unit 310. The right wireless earpiece 302 and the left wireless earpiece 304 may perform separate measurements. The results corresponding to heart rate variability or so forth may be processed, recorded, displayed, logged, or communicated separately or jointly based on the application, user preferences, and so forth. For example, biometric results may be averaged between measurements made by the first radar unit 310 and second radar unit 312 of the set of wireless earpieces 300.

In another embodiment, the first radar unit 310 and the second radar unit 312 may be positioned separately. For example, the first radar unit 310 may broadcast a signal and the second radar unit 312 may receive the reflections (or vice versa). Different transmitting and separating components and positions may enhance effectiveness of the radar while reducing noise and processing difficulties.

In other embodiments, the first radar unit 310 and the second radar unit 312 may represent distinct radar units that utilize distinct signals and target body areas. For example, the first radar unit 310 and the second radar unit 312 may be pointed toward different portions of the ear of the user. For example, the frequency, amplitude, phase, or other characteristics of the signals may be varied as needed to best detect the applicable user biometric or environmental condition. The first and second radar units 310 and 312 may vary the frequency dynamically, based on user input, or so forth.

For example, if the user wearing the right wireless earpiece 304 receives an invitation to establish a connection, the user receiving the invitation may accept the invitation by nodding his head, which may be sensed by the inertial sensors 309, such as an electronic accelerometer via voltage changes due to capacitance differentials caused by the nodding of the head. In addition, the user may tap on or swipe across the gesture interface 306 to bring up a menu from which to send, for example, a preprogrammed reply or one or more pieces of media the third party has selected to share with the user and/or one or more other third parties currently connected to the third party.

The left and right wireless earpiece 302 and 304 may be positioned within the ear canal 307 to minimize the distance between the right wireless earpiece 304 and the user's tympanic membrane 314, such that any sound communications received by the user are effectively communicated to the user using the right wireless earpiece 304.

In another embodiment, externally facing radar may be integrated with the gesture interface 306. The gesture interface 306 may include one or more radar units including LIDAR, RF radar, or so forth. The radar units in the gesture interface 306 may be utilized to sense user input or feedback, such as head motions, hand gestures, or so forth. In another embodiment, the radar units in the gesture interface may sense proximity to other people, vehicles, structures, objects, or so forth. For example, the radar units may detect a vehicle or object that may strike the user from the side (e.g., a blind spot) and may give warnings or alerts (e.g., verbal alert "look to your left", "watch out", beeps in the left wireless earpiece 302, etc.).

Figure 4:
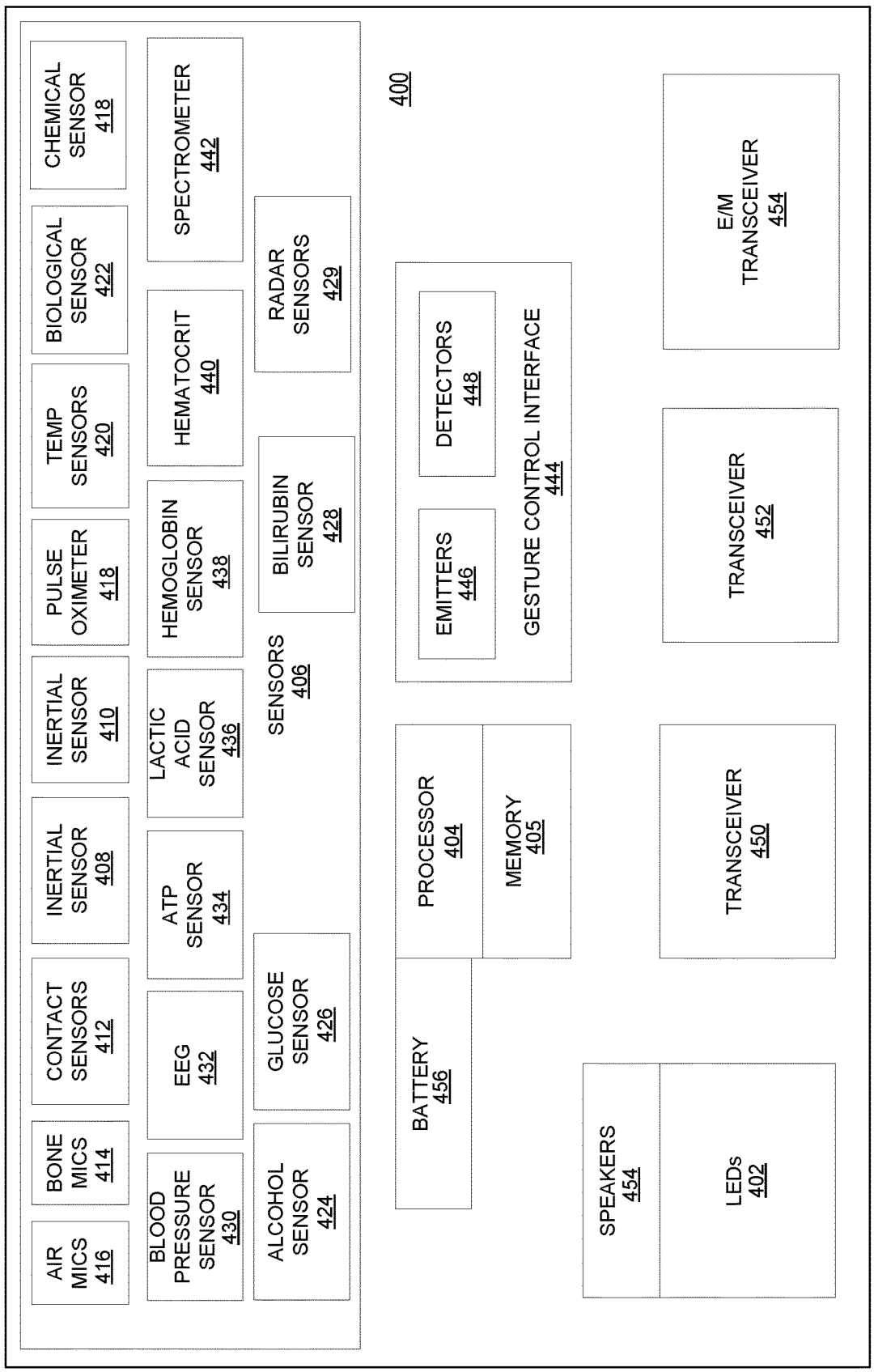
FIG. 4 is a block diagram of wireless earpieces.

FIG. 4 is a block diagram of wireless earpieces 400 in accordance with an illustrative embodiment. The description of the components, structure, functions, units, and other elements of the wireless earpieces 400 may refer to a left wireless earpiece, a right wireless earpiece, or both wireless earpieces 400 as a set or pair. All or a portion of the components shown for the wireless earpieces 400 may be included in each of the wireless earpieces. For example, some components may be included in the left wireless earpiece, but not the right wireless earpiece and vice versa. In another example, the wireless earpieces 400 may not include all the components described herein for increased space for batteries or so forth.

The wireless earpieces 400 are embodiment of wireless earpieces, such as those shown in FIGS. 1-3 (e.g., wireless earpieces 104, 202, 204, 302, 304). The wireless earpieces 400 may represent ear buds, on-ear headphones, or over-ear headphones that may be used jointly or separately. Although not specifically shown, the components of the wireless earpieces 400 are connected utilizing any number of wires, traces, buses, interfaces, pins, ports, connectors, boards, receptacles, chip sets, or so forth.

The wireless earpieces 400 may include one or more light emitting diodes (LEDs) 402 electrically connected to a processor 404 or other intelligent control system. The processor 404 is the logic that controls the operation and functionality of the wireless earpieces 400. The processor 404 may include circuitry, chips, and other digital logic. The processor 404 may also include programs, scripts, and instructions that may be implemented to operate the various components of the wireless earpieces 400.

The processor 404 may represent hardware, software, firmware, or any combination thereof. In one embodiment, the processor 404 may include one or more processors or logic engines. For example, the processor 404 may represent an application specific integrated circuit (ASIC) or field programmable gate array (FPGA). The processor 404 may utilize information from the sensors 406 to determine the biometric information, data, and readings of the user. The processor 404 may utilize this information and other criteria to inform the user of the biometrics (e.g., audibly, through an application of a connected device, tactilely, etc.) as well as communicate with other electronic devices wirelessly through the transceivers 450, 452, 454.

The processor 404 may also process user input to determine commands implemented by the wireless earpieces 400 or sent for processing through the transceivers 450, 452, 454. Specific actions may be associated with biometric data thresholds. For example, the processor 404 may implement a macro allowing the user to associate biometric data as sensed by the sensors 406 with specified commands, user actions, responses, alerts, and so forth. In one example, if the wireless earpieces 400 determine the user has been struck based on feedback from the sensors 406, the user may be asked to verify her physical status and condition to ensure her well-being. A negative response or no response over a period of time may be utilized to send an emergency communication requesting help or other assistance. In another example, if the temperature of the user is above or below high and low thresholds, an audible alert may be played to the user and a communication sent to an associated medical device for communication to one or more medical professionals. In one embodiment, the processor 404 may process radar data to identify user biometrics (e.g. blood pressure, heart rate variability, blood velocity, ear/head structure, etc.), external conditions (e.g., approaching objects, user proximity to structures, people, objects, etc.), and other applicable information.

A memory 405 is a hardware element, device, or recording media configured to store data or instructions for subsequent retrieval or access at a later time. The memory 405 may represent static or dynamic memory. The memory 405 may include a hard disk, random access memory, cache, removable media drive, mass storage, or configuration suitable as storage for data, instructions, and information. In one embodiment, the memory 405 and the processor 404 may be integrated. The memory may use any type of volatile or non-volatile storage techniques and mediums. The memory 405 may store information related to the status of a user, wireless earpieces 400, interconnected electronic device, and other peripherals, such as a wireless device, smart glasses, smart watch, smart case for the wireless earpieces 400, wearable device, and so forth. In one embodiment, the memory 405 may display instructions, programs, drivers, or an operating system for controlling the user interface including one or more LEDs or other light emitting components, speakers, tactile generators (e.g., vibrator), and so forth. The memory 405 may also store the thresholds, conditions, or biometric data (e.g., biometric and data library) associated with biometric events.

The processor 404 may also be electrically connected to one or more sensors 406. In one embodiment, the sensors 406 may include inertial sensors 408, 410 or other sensors that measure acceleration, angular rates of change, velocity, and so forth. For example, each inertial sensor 408, 410 may include an accelerometer, a gyro sensor or gyrometer, a magnetometer, a potentiometer, or other type of inertial sensor.

The sensors 406 may also include one or more contact sensors 412, one or more bone conduction microphones 414, one or more air conduction microphones 416, one or more chemical sensors 418, a pulse oximeter 418, a temperature sensor 420, or other physiological or biological sensors 422. Further examples of physiological or biological sensors 422 include an alcohol sensor 424, glucose sensor 426, or bilirubin sensor 428. Other examples of physiological or biological sensors 422 may also be included in the wireless earpieces 402. These may include a blood pressure sensor 430, an electroencephalogram (EEG) 432, an Adenosine Triphosphate (ATP) sensor 434, a lactic acid sensor 436, a hemoglobin sensor 438, a hematocrit sensor 440, or other biological or chemical sensor. In some embodiments, the sensors 406 embedded in the wireless earpieces may be limited to basic sensors, such as contact sensors 412, bone conduction microphones 414, air conduction microphones 416, and radar sensors 429.

In one embodiment, the wireless earpieces 400 may include radar sensors 429. As described herein, the radar sensors 429 may be positioned to look toward the user wearing the wireless earpieces 400 or external to or away from the wireless earpieces 400. The radar sensors 429 may be configured to perform analysis or may capture information, data, and readings in the form of reflected signals that may be processed by the processor 404. The radar sensors 429 may include Doppler radio, laser/optical radar, or so forth. The radar sensors 429 may be configured to perform measurements regardless of whether the wireless earpieces 400 are being worn or not. In one embodiment, the wireless earpieces 400 may include a modular radar unit that may be added to or removed from the wireless earpieces 400. In other embodiments, a modular sensor unit may include the sensors 406 and may be removed, replaced, exchanged, or so forth. The modular sensor unit may allow the wireless earpieces 400 to be adapted for specific purposes, functionality, or needs. For example, the modular sensor unit may have contacts for interfacing with the other portions of the components. The modular sensor unit may have an exterior surface that contacts the ear skin or tissue of the user for performing direct measurements.

In one embodiment, the radar sensors 429 may represent time-of-flight cameras or sensors. The time-of-flight camera may resolve distances For example, the time-of-flight camera utilized as part of the radar sensors 429 may include an illumination unit (e.g., RF-modulated LEDs or laser diodes), optics (e.g., one or more lenses, focal plane arrays, optical filters, etc.), image sensors, driver electronics, and computation logic or processor 404.

In one embodiment, the radar sensors 429 may be encompassed entirely within a frame of the wireless earpieces 400. The radar sensors 429 may also be entirely or partially enclosed by the frame to prevent dust, sweat, dirt, water, or other contaminants from damaging the radar sensors 429. In one embodiment, the radar sensors 429 may include a first set of radar sensors for internal user radar measurements of pulsatile measurements, including, but not limited to, heart rate, heart rate variability, blood flow velocity, blood pressure, and respiration rate, and a second set of radar sensors for external radar measurements (e.g., environment, objects, proximate parties, structures, etc.). In one embodiment, the radar sensors 429 may generate a composite signal from the readings performed. A Doppler frequency of blood flow and other pulsatile measurements (e.g., heart rate, heart rate variability, blood flow velocity) may be determined from the composite signal.

The radar sensors 429 may determine the orientation and motion of the wireless earpieces 400 with regard to one another as well as the user's head/body. The radar sensors 429 may also determine the distance between the wireless earpieces 400. The radar sensors 429 may also identify a user utilizing the wireless earpieces 400 to determine whether it is an authorized/registered user or a guest, unauthorized user, or other party. The radar signature for each user may vary based on the user's ear, head, and body shape and may be utilized to perform verification and identification. For example, a baseline radar signature may be determined during a training or registration process that may be utilized by the wireless earpieces 400 (or other wireless earpieces) to identify the user. Information measured or determined by the radar sensors 429 may be communicated utilizing audio, visual (e.g., LED, associated wireless device, etc.), tactile, or electrical alerts. The alerts may be sent based on specified events, thresholds, activities or so forth. For example, if the heart rate variability exceeds a threshold an alert may be sent to the user and any other third party A spectrometer 442 is also shown. The spectrometer 442 may be an infrared (IR) through ultraviolet (UV) spectrometer although it is contemplated that any number of wavelengths in the infrared, visible, or ultraviolet spectrums may be detected (e.g., X-ray, gamma, millimeter waves, microwaves, radio, etc.). In one embodiment, the spectrometer 442 is adapted to measure environmental wavelengths for analysis and recommendations, and thus, may be located or positioned on or at the external facing side of the wireless earpieces 400.

A gesture control interface 444 is also operatively connected to the processor 404. The gesture control interface 444 may include one or more emitters 446 and one or more detectors 448 for sensing user gestures. The emitters 446 may be of any number of types including infrared LEDs, lasers, and visible light. As noted, in one embodiment, the gesture control interface 444 may include some of the radar sensors 429 as well for externally processing user input, environmental conditions, user activities, and so forth.

The wireless earpieces may also include a number of transceivers 450, 452, 454. The transceivers 450, 452, 454 are components including both a transmitter and receiver which may be combined and share common circuitry on a single housing. The transceivers 450, 452, 454 may communicate utilizing Bluetooth, Wi-Fi, NFMI, ZigBee, Ant+, near field communications, wireless USB, infrared, mobile body area networks, ultra-wideband communications, cellular (e.g., 3G, 4G, 5G, PCS, GSM, etc.), infrared, or other suitable radio frequency standards, networks, protocols, or communications. The transceivers 450, 452, 454 may also be a hybrid transceiver that supports a number of different communications. For example, the transceiver 450, 452, 454 may communicate with other electronic devices or other systems utilizing wired interfaces (e.g., wires, traces, etc.), NFC or Bluetooth communications. For example, a transceiver 450 may allow for induction transmissions between wireless earpieces 400 or other devices utilizing near field magnetic induction (NFMI).

Another transceiver 452 may utilize any number of short-range communications signals, standards or protocols (e.g., Bluetooth, BLE, UWB, etc.), or other form of radio communication may also be operatively connected to the processor 404. The transceiver 452 may be utilized to communicate with any number of communications, computing, or network devices, systems, equipment, or components. The transceiver 452 may also include one or more antennas for sending and receiving signals.

In one embodiment, the transceiver 454 may be a magnetic induction electric conduction electromagnetic (E/M) transceiver or other type of electromagnetic field receiver or magnetic induction transceiver that is also operatively connected to the processor 404 to link the processor 404 to the electromagnetic field of the user. For example, the use of the transceiver 454 allows the device to link electromagnetically into a personal area network, body area network, or other device.

In operation, the processor 404 may be configured to convey different information using one or more of the LEDs 402 based on context or mode of operation of the device. The various sensors 406, the processor 404, and other electronic components may be located on the printed circuit board of the device. One or more speakers 454 may also be operatively connected to the processor 404.

The wireless earpieces 400 may include a battery 456 that powers the various components to perform the processes, steps, and functions herein described. The battery 456 is one or more power storage devices configured to power the wireless earpieces 400. In other embodiments, the battery 208 may represent a fuel cell, thermal electric generator, piezo electric charger, solar charger, ultra-capacitor, or other existing or developing power storage technologies.

Although the wireless earpieces 400 shown includes numerous different types of sensors and features, it is to be understood that each wireless earpiece need only include a basic subset of this functionality. It is further contemplated that sensed data may be used in various ways depending upon the type of data being sensed and the particular application(s) of the earpieces.

As shown, the wireless earpieces 400 may be wirelessly linked to any number of wireless or computing devices (including other wireless earpieces) utilizing the transceivers 450, 452, 454. Data, user input, feedback, and commands may be received from either the wireless earpieces 400 or the computing device for implementation on either of the devices of the wireless earpieces 400 (or other externally connected devices). As previously noted, the wireless earpieces 400 may be referred to or described herein as a pair (wireless earpieces) or singularly (wireless earpiece). The description may also refer to components and functionality of each of the wireless earpieces 202 collectively or individually.

In some embodiments, linked or interconnected devices may act as a logging tool for receiving information, data, or measurements made by the wireless earpieces 400. For example, a linked computing device may download data from the wireless earpieces 400 in real-time. As a result, the computing device may be utilized to store, display, and synchronize data for the wireless earpieces 400. For example, the computing device may display pulse rate, blood oxygenation, blood pressure, blood flow velocity, heart rate variability, temperature, and so forth as measured by the wireless earpieces 400. In this example, the computing device may be configured to receive and display alerts that indicate a specific health event or condition has been met. For example, if the forces applied to the sensors 406 (e.g., accelerometers) indicate that the user may have experienced a concussion or serious trauma, the wireless earpieces 400 may generate and send a message to the wireless or computing device. The wireless earpieces 400 may have any number of electrical configurations, shapes, and colors and may include various circuitry, connections, and other components.

The components of the wireless earpieces 400 may be electrically interconnected utilizing any number of wires, contact points, leads, busses, wireless interfaces, or so forth. In addition, the wireless earpieces 400 may include any number of computing and communications components, devices or elements which may include busses, motherboards, circuits, chips, sensors, ports, interfaces, cards, converters, adapters, connections, transceivers, displays, antennas, and other similar components.

The wireless earpieces 400 may also include physical interfaces (not shown) for connecting the wireless earpieces with other electronic devices, components, or systems, such as a smart case or wireless device. The physical interfaces may include any number of contacts, pins, arms, or connectors for electrically interfacing with the contacts or other interface components of external devices or other charging or synchronization devices. For example, the physical interface may be a micro USB port. In one embodiment, the physical interface is a magnetic interface that automatically couples to contacts or an interface of the computing device. In another embodiment, the physical interface may include a wireless inductor for charging the wireless earpieces 400 without a physical connection to a charging device.

As originally packaged, the wireless earpieces 400 may include peripheral devices such as charging cords, power adapters, inductive charging adapters, solar cells, batteries, lanyards, additional light arrays, speakers, smart case covers, transceivers (e.g., Wi-Fi, cellular, etc.), or so forth.

Figure 5:
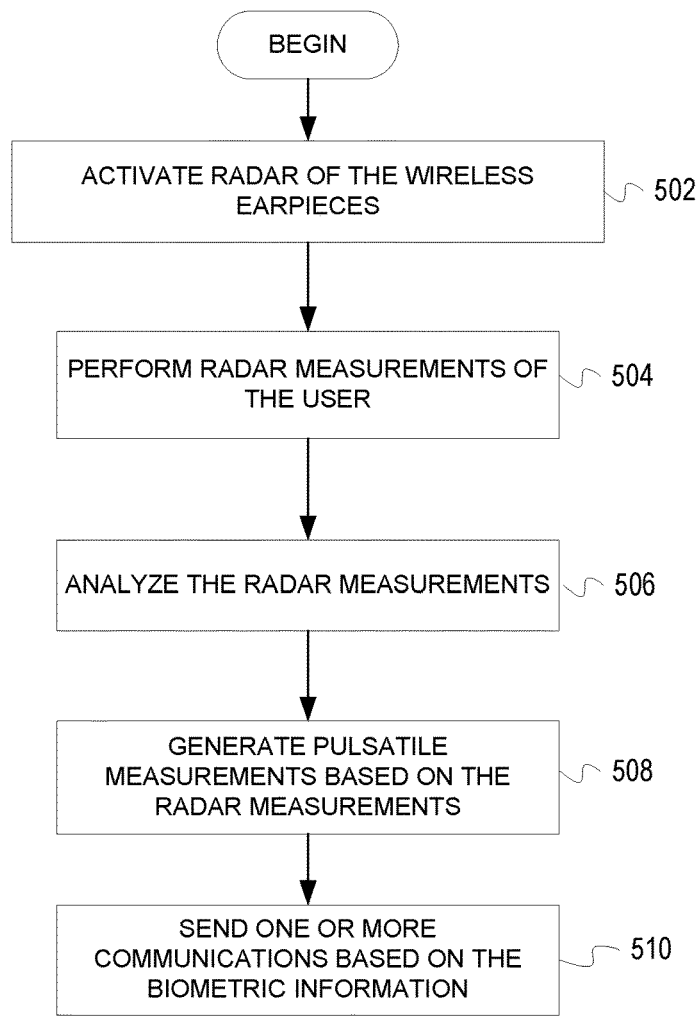
FIG. 5 is a flowchart of a process for performing radar measurements of a user utilizing wireless earpieces.

FIG. 5 is a flowchart of a process for performing radar measurements of a user utilizing wireless earpieces in accordance with illustrative embodiments. In one embodiment, the process of FIGS. 5-7 may be implemented by one or more wireless earpieces worn by a user (e.g., wireless earbuds, over-ear headphones, on-ear headphones, etc.). In another embodiment, the wireless earpieces need not be worn to be utilized.

In one embodiment, the process begins by activating radar of the wireless earpieces (step 502). The radar may represent Doppler or optical radar utilizing any number of signals (e.g., pulse, continuous, etc.). In one embodiment, the radar sensors or units of the wireless earpieces may be activated whenever the wireless earpieces are turned on (e.g., not in a power save, low power, or charging mode). In other embodiments, a specific function, application, user request, or other automated or manual process may initiate, power-on, or otherwise activate the radar of the wireless earpieces. In one embodiment, the radar sensors of the wireless earpieces worn in-ear may be positioned within the external auditory canal. In another embodiment, the radar sensors of the wireless earpieces may be integrated in headphones worn by the user and may read measurements from the user's ear, neck, head, or other portions of the body of the user.

Next, the wireless earpieces perform radar measurements of the user (step 504). Each of the wireless earpieces may include one or more radar sensors or units performing radar measurements. In one embodiment, each radar unit may send a signal and receive back the reflections. In another embodiment, distinct radar units (whether within a single wireless earpiece or utilized between the different wireless earpieces) may send radar signals and receive the reflections or echoes. In one embodiment, the radar sensors may be directed toward one or more different portions of the user's ear, head, or body.

Next, the wireless earpieces analyze the radar measurements (step 506). The radar measurements may be analyzed or otherwise processed by a logic engine or processor. In one embodiment, the radar measurements are utilized to determine pulsatile measurements, such as heart rate, change in heart rate, blood flow velocity, and so forth. The measurements parameters may also include motion, such as rotation, displacement, deformation, acceleration, fluid-flow velocity, vortex shedding Poiseulle's law of fluid flow, Navier Stoke's equations, and so forth. For example, the radar sensors may measure the displacement of vessel walls. The radar sensors may measure the movement and volume of the residual component of the external auditory canal. The measurements may be detected in the received signal. The radar measurements may be converted to data, information, values, graphics, charts, visuals, or other information that may be communicated audibly through the wireless earpieces to a communications or computing devices. For example, biometric information, values, and data retrieved through analysis may be communicated to the user. During step 506, the radar sensors may detect changes in the received/reflected signal to determine amplitude, phase, phase angle and other applicable information (e.g., backscatter analysis). The analysis may determine the position, location, and orientation of the user and the wireless earpieces relative to each other and the user.

Next, the wireless earpieces generate pulsatile measurements based on the radar measurements (step 508). The pulsatile measurements may relate to the operation of the heart/body of the user and may include extensive biometric information. The biometric information may be generated from each of the wireless earpieces or may represent combined measurements from multiple wireless earpieces including one or more radar sensors/units. The biometric information may include heart rate, heart rate variability, blood flow velocity, blood oxygenation, blood pressure, stridor level, cerebral edema, respiration rate, excretion levels, ear/face/body structure, and other user biometrics. For example, the radar sensors may detect any number of biometrics or conditions associated with blood flow or changes in blood flow. The wireless earpieces may utilize any number of mathematical, signal processing, filtering, or other processes to generate the biometric information. The radar sensors may be utilized in conjunction with accelerometers, gyroscopes, thermistors, optical sensors, magnetometers, pressure sensors, environmental sensors, microphones, and so forth.

Next, the wireless earpieces send one or more communications based on the biometric information (step 510). The wireless earpieces may communicate the biometric information utilizing audible notices (e.g., your heart rate variability is _____, your blood pressure is _____, etc.), sounds, alerts, tactile feedback, light emissions (e.g., LEDs, touch screens, etc.). The communications may be to the user wearing the wireless earpieces or to specified users and devices.

Figure 6:
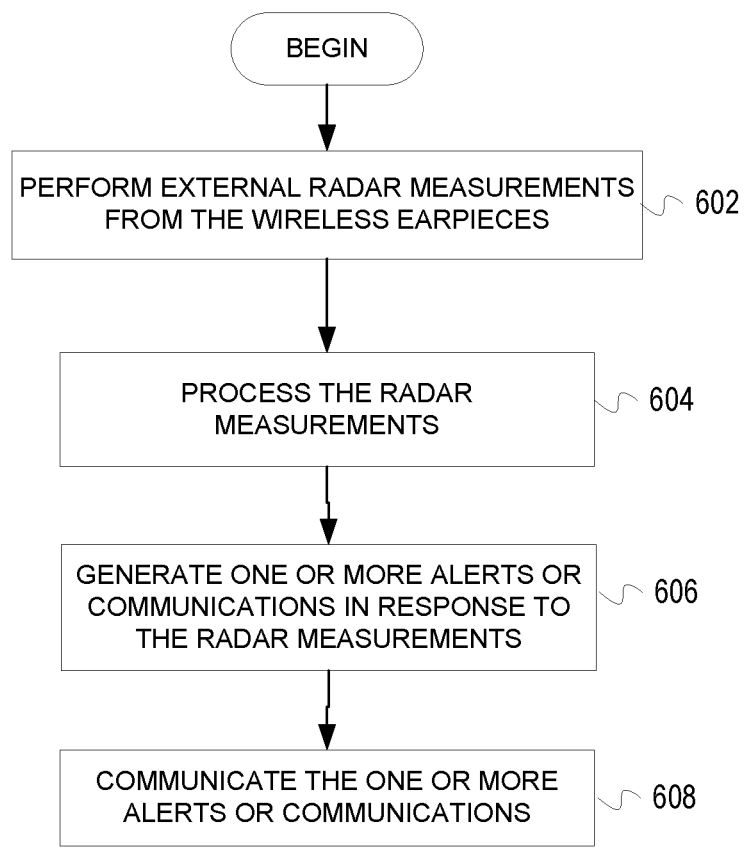
FIG. 6 is a flowchart of a process for generating alerts in response to external radar measurements performed by the wireless earpieces.

FIG. 6 is a flowchart of a process for generating alerts in response to external radar measurements performed by the wireless earpieces. In one embodiment, the process of FIG. 6 may be implemented utilizing one or more externally facing radar sensors/units within the wireless earpieces. For example, the touch/gesture interface may include Doppler radar sensors, LIDAR, TOF cameras, or other similar radar units. All or portions of the processes described in FIGS. 5 and 6 (as well as the other included Figures and description) may be combined in any order, step, or any potential iteration.

The process of FIG. 6 may begin by performing external radar measurements from the wireless earpieces (step 602). As previously described, the wireless earpieces may each include one or more internal and externally facing radar sensors. The radar sensors may be utilized to protect the user and document incoming people or objects as well as associated events, such as wrecks, crashes, collisions, contact, proximity alerts, near misses, and so forth. The external radar sensors may be fixedly positioned or may dynamically move toward a specific direction utilizing any number of motors, actuators, and so forth.

Next, the wireless earpieces process the radar measurements (step 604). In one embodiment, the wireless earpieces may utilize internal processors, logic, circuits, or so forth to process the radar measurements. The radar sensors/units may also be configured to dynamically adjust signals based on the conditions, user, environment, noise levels, and so forth and to correspondingly process the radar measurements. During step 604, the radar measurements may be processed for communication or display by the wireless earpieces or any number of other devices in communication with the wireless earpieces. For example, the radar measurements may include biometric readings, such as pulsatile measurements, wireless earpiece position, orientation, and motion (e.g., relative to the user, each other, etc.).

During step 604, the wireless earpieces may determine whether there is a condition or event that should be communicated to the user/connected device, logged, recorded, or streamed, or otherwise processed. In one embodiment, user preferences, settings, parameters, thresholds, conditions, or other information may be utilized to determine whether an action should be performed. For example, the radar sensors may determine that the user may have fallen based on the detected motion of the user's head, that a user is about to be struck by a vehicle (e.g., car, bicycle, etc.), that the user is proximate a wall or other object, or any number of other activities.

Next, the wireless earpieces generate one or more alerts or communications in response to the radar measurements (step 606). The alerts or communications may also be communicated based on a user request, user preferences, or so forth. The alerts or communications may represent alerts, messages, tactile feedback, sounds, or audio communicated by the wireless earpieces or text messages, in-app communications, streaming content, packets, or other alerts or communications sent from the wireless earpieces to any number of other users/devices (directly or indirectly).

Next, the wireless earpieces communicate the one or more alerts or communications (step 608). The one or more alerts or communications may be sent directly (e.g., utilizing Bluetooth, Wi-Fi, NFMI, etc.), or through any number of networks or devices (e.g., Wi-Fi, LAN, cellular networks, cloud networks, mesh networks, etc.). In one embodiment, a receiving device may perform a specified activity based on the alert or communication. For example, a vehicle may prepare for a collision by tightening the seatbelts, braking, swerving, flashing lights, preparing or firing airbags, or so forth. In another example, the alert may indicate to one or more designated parties that the user may have been injured (e.g., concussion, trauma, etc.). The wireless earpieces may also warn the user "watch out on your left" or any number of other applicable audio warnings. In one embodiment, the communications may include a command or instruction to a connected device. For example, a helmet worn by the user may cinch up or inflate one or more pouches/bags in response to determining a collision may be imminent.

Figure 7:
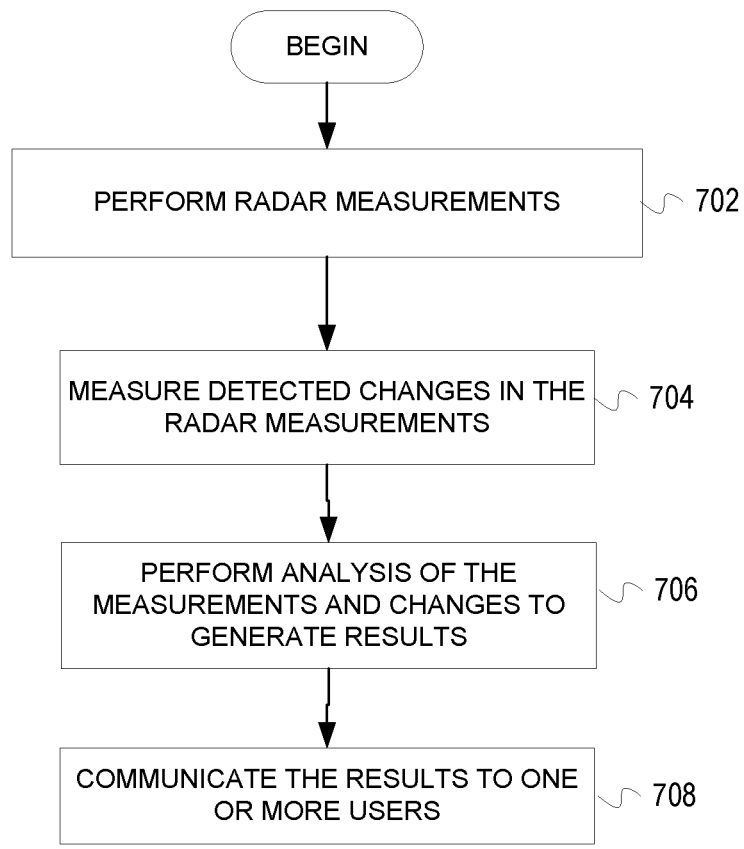
FIG. 7 is a flowchart of a process for performing radar measurements.

FIG. 7 is a flowchart of a process for performing radar measurements in accordance with an illustrative embodiment. The process may begin by performing radar measurements (step 702). In one embodiment, the radar measurements are pulse based active radar measurements. The radar measurements may be focused at the user wearing the wireless earpieces. The radar measurements may also be applicable to the environment of the user, people surrounding the user, and so forth. The measurements made during step 702 may represent initial measurements performed by the wireless earpieces. The radar sensors of the wireless earpieces may be beneficial because of their insensitivity to ambient light, skin pigmentation, user contact/interaction, electronic/environmental noise, and so forth. In some embodiments, the radar sensors may be entirely embedded within the wireless earpieces to shield the sensors from sweat/bodily fluids, water, dirt, dust, particulates, and other materials.

In one embodiment, the wireless earpieces may perform Doppler measurements of blood flow, displacement of vessel walls, and/or movement/volume of the residual component of the external auditory canal. For example, the Doppler-frequency of the blood flow velocity may be determined for detectable flow velocities. In one embodiment, the radar measurements may be utilized to identify the ear, head, or body of the user. For example, a unique radar signature (e.g., structure of the inner/outer ear, cheek, jaw bone, bone structure of the head, body musculature, etc.) may be associated with each user. The unique radar signature may be saved as part of a user profile, settings, or other biometric information and may be utilized to subsequently identify or authenticate the user for future usage of the wireless earpieces. For example, user authentication may be utilized to determine the features, functions, contacts, and other data that is available to the user based on the authentication and authorizations that may be performed utilizing the radar signature determined during step 702. In another embodiment, the radar measurements may also determine where the wireless earpieces are being worn, stored, or so forth. For example, the radar measurements may determine placement in an ear of the user, placed on a desk/counter/surface, charging in a smart charger, or so forth.

Next, the wireless earpieces measure detected changes in the radar measurements (step 704). The changes may be utilized to determine changes in the biometrics of the user, environmental conditions, and so forth. The changes may measure changes in amplitude, phase, detected phase angle, and other aspects of the received or reflected signal. The biometrics of the user may include pulse rate, heart rate variability, blood flow velocity, blood pressure, pulse oximetry (SpO2), respiration rate, Stridor level, cerebral edema, and other central nervous system (CNS) acute phenomena). For example, changes in blood flow may change the radar signature of the user being measured as compared to baseline parameters.

Next, the wireless earpieces perform analysis of the measurements and changes to generate results (step 706). The analysis of the measurements may include an amplitude of the received signals. For example, the wireless earpieces may utilize backscatter from the active signals. The wireless earpieces may measure amplitude, phase (e.g., offset, difference, angle, etc.), and other information of the received signals. The results may indicate the location of the user, proximity to users, buildings, or other objects, location of a paired or associated device (e.g., position, orientation, distances, etc.), motion relative to the user, buildings, or other objects, and so forth. For example, distances, relative motion, and orientation between paired devices, such as the wireless earpieces and a cell phone or a wireless headset and a tablet may be determined.

The analysis may include combining multiple sensor measurements. For example, sensor measurements from accelerometers, thermistors, optical sensors, photoreceptors, magnetometers, gyroscopes, pressure sensors, environmental nanoparticle sensors, and any number of sensors.

Next, the wireless earpieces communicate the results to one or more users (step 708). The results may be played, displayed, or otherwise communicated to the user of the wireless earpieces or one or more designated users, devices, systems, equipment, interfaces, websites, servers, or so forth. The user preferences or other information may specify how, when, and where the results are communicated.

A system, method, and wireless earpieces are provided for performing radar measurements. The radar sensors of the wireless earpieces may be internally or externally directed. Any number of pulse, pattern, active, passive, or continuous signal radar systems may be utilized. The radar sensors may be utilized to measure a physiological parameter from which information, such as hear rate based on the movement (displacement) of blood within the veins, arteries, tissues, or skin of the user's ear. The radar sensors may also measure the movement or displacement of the vessel walls, movement of the residual component of the external auditory canal, and so forth. The radar measurements may be effective even in the presence of sweat, water, dirt, dust, or during strenuous physical activities.

In one embodiment, the wireless earpieces may utilize radar measurements to determine their relative location to other devices (e.g., paired, associated, communicating electronic devices, detectable, etc.), the user, structures, objects, or so forth.

The features, steps, and components of the illustrative embodiments may be combined in any number of ways and are not limited specifically to those described. In particular, the illustrative embodiments contemplate numerous variations in the smart devices and communications described. The foregoing description has been presented for purposes of illustration and description. It is not intended to be an exhaustive list or limit any of the disclosure to the precise forms disclosed. It is contemplated that other alternatives or exemplary aspects are considered included in the disclosure. The description is merely examples of embodiments, processes or methods of the invention. It is understood that any other modifications, substitutions, and/or additions may be made, which are within the intended spirit and scope of the disclosure. For the foregoing, it can be seen that the disclosure accomplishes at least all of the intended objectives.

The previous detailed description is of a small number of embodiments for implementing the invention and is not intended to be limiting in scope. The following claims set forth a number of the embodiments of the invention disclosed with greater particularity.

What is claimed is:

1. A wireless earpiece, comprising:
an earpiece housing for fitting in an ear of a user;
a processor controlling functionality of the wireless earpiece;
a plurality of sensors perform sensor measurements of the user, wherein the plurality of sensors include one or more radar sensors;
a transceiver capable of communicating with at least a wireless device;
wherein the processor activates the one or more radar sensors to perform radar measurements, and analyzes the radar measurements to determine pulsatile measurements associated with the user;
wherein the one or more radar sensors include an internally facing radar sensor and an externally facing radar sensor and wherein the internally facing radar sensor is positioned for performing the radar measurements used to determine the pulsatile measurements associated with the user and wherein the externally facing radar sensor is positioned for determining user gestures.

2. The wireless earpiece of claim 1, wherein the processor compares a baseline radar signature of the user with a radar signature read by the one or more radar sensors to identify the user.

3. The wireless earpiece of claim 1, wherein the pulsatile measurements include one or more of heart rate, heart rate variability, blood flow velocity, blood pressure, and respiration rate.

4. The wireless earpiece of claim 1, wherein the processor isolates a Doppler frequency of a blood flow velocity from a composite signal represented by the radar measurements.

5. The wireless earpiece of 1, wherein the processor determines the motion of the wireless earpiece, and positioning of the wireless earpiece relative to a head of the user.

6. A wireless earpiece, comprising:
an earpiece housing adapted to fit into an ear of a user;
a processor for executing a set of instructions, the processor disposed within the earpiece housing;
at least one radar sensor operatively connected to the processor;
a memory operatively connected to the processor for storing the set of instructions, wherein the instructions are executed to:
activate one or more of the at least one radar sensors of the wireless earpieces, perform radar measurements of the user, and analyze the radar measurements to determine pulsatile measurements associated with the user;
wherein the at least one radar sensor includes an internally facing radar sensor and an externally facing radar sensor and wherein the internally facing radar sensor is positioned for performing the radar measurements used to determine the pulsatile measurements associated with the user and wherein the externally facing radar sensor is positioned for determining user gestures.

7. The wireless earpiece of claim 6 wherein the pulsatile measurements are blood velocity measurements.

8. The wireless earpiece of claim 7 wherein the processor isolates a Doppler frequency of a blood flow velocity from a composite signal represented by the radar measurements in determining the blood velocity measurements.

* * * * *